(12) United States Patent
Yamanaka et al.

(10) Patent No.: US 9,404,868 B2
(45) Date of Patent: Aug. 2, 2016

(54) MEASURING DEVICE, MEASURING SYSTEM, MEASURING METHOD, CONTROL PROGRAM, AND RECORDING MEDIUM

(75) Inventors: Mikihiro Yamanaka, Osaka (JP); Megumi Hijikuro, Osaka (JP); Keita Hara, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 456 days.

(21) Appl. No.: 13/821,464

(22) PCT Filed: Sep. 7, 2011

(86) PCT No.: PCT/JP2011/070402
§ 371 (c)(1),
(2), (4) Date: Mar. 7, 2013

(87) PCT Pub. No.: WO2012/033139
PCT Pub. Date: Mar. 15, 2012

(65) Prior Publication Data
US 2013/0168573 A1    Jul. 4, 2013

(30) Foreign Application Priority Data
Sep. 9, 2010   (JP) ................. 2010-202209

(51) Int. Cl.
*G01N 21/64* (2006.01)
*A61B 5/00* (2006.01)
*A61B 5/145* (2006.01)

(52) U.S. Cl.
CPC .......... *G01N 21/6486* (2013.01); *A61B 5/0071* (2013.01); *A61B 5/14546* (2013.01); *A61B 5/489* (2013.01); *G01N 21/6456* (2013.01); *G01N 2021/6417* (2013.01)

(58) Field of Classification Search
CPC .......... G01N 21/64; G01N 2021/6415; G01N 2021/6419; G01N 2021/6423; G01N 2021/6421
USPC ..................... 250/365, 372, 461.1
See application file for complete search history.

(56) References Cited

U.S. PATENT DOCUMENTS 5,539,517 A   7/1996   Cabib et al.
5,655,530 A   8/1997   Messerschmidt
(Continued)

FOREIGN PATENT DOCUMENTS

JP   11-500832 A    1/1999
JP   2002-521685 A  7/2002
(Continued)

OTHER PUBLICATIONS

International Search Report issued in PCT/JP2011/070402, dated Dec. 20, 2011.
(Continued)

*Primary Examiner* — David Porta
*Assistant Examiner* — Djura Malevic
(74) *Attorney, Agent, or Firm* — Birch, Stewart, Kolasch & Birch, LLP.

(57) ABSTRACT

A measuring device (9) of the present invention includes a detector control module (31) for obtaining, from a scanning mechanism including an excitation light source (4) for emitting excitation light and a detector (8) for receiving fluorescence generated from the measurement target upon irradiation with the excitation light, measurement data of the fluorescence, a position information obtaining module (32) for obtaining, from a driving mechanism for controlling relative positions of the scanning mechanism and the measurement target, information of a position where the measurement target is irradiated with the excitation light when the measurement data is obtained, and a fluorescence characteristic management module (33) for preparing fluorescence characteristic data including the measurement data and the position information.

13 Claims, 18 Drawing Sheets

(56) References Cited

U.S. PATENT DOCUMENTS

| | | |
|---|---|---|
| 5,719,024 A | 2/1998 | Cabib et al. |
| 5,784,162 A | 7/1998 | Cabib et al. |
| 5,798,262 A | 8/1998 | Garini et al. |
| 5,817,462 A | 10/1998 | Garini et al. |
| 5,823,951 A | 10/1998 | Messerschmidt |
| 5,835,214 A | 11/1998 | Cabib et al. |
| 5,856,871 A | 1/1999 | Cabib et al. |
| 5,871,932 A | 2/1999 | Bar-Am et al. |
| 5,906,919 A | 5/1999 | Garini et al. |
| 5,912,165 A | 6/1999 | Cabib et al. |
| 5,936,731 A | 8/1999 | Cabib et al. |
| 5,991,028 A | 11/1999 | Cabib et al. |
| 5,995,645 A | 11/1999 | Soenksen et al. |
| 6,007,996 A | 12/1999 | McNamara et al. |
| 6,018,587 A | 1/2000 | Cabib |
| 6,043,039 A | 3/2000 | Bar-Am et al. |
| 6,055,325 A | 4/2000 | Garini et al. |
| 6,066,459 A | 5/2000 | Garini et al. |
| 6,075,599 A | 6/2000 | Milman et al. |
| 6,152,876 A | 11/2000 | Robinson et al. |
| 6,165,734 A | 12/2000 | Garini et al. |
| 6,198,532 B1 | 3/2001 | Cabib et al. |
| 6,212,424 B1 | 4/2001 | Robinson |
| 6,240,306 B1 | 5/2001 | Rohrscheib et al. |
| 6,276,798 B1 | 8/2001 | Gil et al. |
| 6,556,853 B1 | 4/2003 | Cabib et al. |
| 6,622,032 B1 | 9/2003 | Robinson et al. |
| 6,690,817 B1 | 2/2004 | Cabib et al. |
| 6,865,408 B1 | 3/2005 | Abbink et al. |
| 2001/0018560 A1 | 8/2001 | Robinson |
| 2001/0033364 A1 | 10/2001 | Cabib et al. |
| 2002/0035341 A1 | 3/2002 | Rohrscheib et al. |
| 2003/0007147 A1 | 1/2003 | Johnson |
| 2003/0020022 A1 | 1/2003 | Kuwabata et al. |
| 2003/0023152 A1 | 1/2003 | Abbink et al. |
| 2003/0023170 A1 | 1/2003 | Gardner et al. |
| 2003/0191378 A1 | 10/2003 | Davis, III et al. |
| 2004/0082070 A1 | 4/2004 | Jones et al. |
| 2004/0167382 A1 | 8/2004 | Gardner et al. |
| 2005/0090750 A1 | 4/2005 | Ediger et al. |
| 2005/0148834 A1 | 7/2005 | Hull et al. |
| 2005/0261560 A1 | 11/2005 | Ridder et al. |
| 2006/0167349 A1 | 7/2006 | Gardner et al. |
| 2006/0173256 A1 | 8/2006 | Ridder et al. |
| 2006/0178570 A1 | 8/2006 | Robinson et al. |
| 2006/0211928 A1 | 9/2006 | Hull et al. |
| 2007/0073118 A1 | 3/2007 | Ridder et al. |
| 2007/0088205 A1 | 4/2007 | Hull et al. |
| 2007/0142720 A1 | 6/2007 | Ridder et al. |
| 2007/0197880 A1 | 8/2007 | Maynard et al. |
| 2007/0265532 A1 | 11/2007 | Maynard et al. |
| 2007/0276199 A1 | 11/2007 | Ediger et al. |
| 2008/0097174 A1 | 4/2008 | Maynard et al. |
| 2008/0103373 A1 | 5/2008 | Matter et al. |
| 2008/0103396 A1 | 5/2008 | Johnson et al. |
| 2008/0208018 A1 | 8/2008 | Ridder et al. |
| 2008/0319286 A1 | 12/2008 | Ridder et al. |
| 2009/0003764 A1 | 1/2009 | Ridder et al. |
| 2009/0018415 A1 | 1/2009 | Robinson et al. |
| 2009/0234204 A1 | 9/2009 | Ridder et al. |
| 2010/0010325 A1 | 1/2010 | Ridder et al. |
| 2011/0178420 A1 | 7/2011 | Ridder et al. |
| 2011/0184260 A1 | 7/2011 | Robinson et al. |
| 2011/0282167 A1 | 11/2011 | Ridder et al. |
| 2012/0065484 A1 | 3/2012 | Hull et al. |
| 2012/0078075 A1 | 3/2012 | Maynard et al. |
| 2012/0078473 A1 | 3/2012 | Ridder et al. |
| 2012/0179010 A1 | 7/2012 | Maynard et al. |
| 2012/0190945 A1 | 7/2012 | Yamanaka et al. |
| 2012/0197096 A1 | 8/2012 | Ridder et al. |
| 2012/0283531 A1 | 11/2012 | Maynard et al. |
| 2012/0326055 A1 * | 12/2012 | Wilson ................ A61B 5/0059 250/459.1 |
| 2013/0030306 A1 | 1/2013 | Yamanaka et al. |

FOREIGN PATENT DOCUMENTS

| | | |
|---|---|---|
| JP | 2003-28797 A | 1/2003 |
| JP | 2004-125605 A | 4/2004 |
| JP | 2007-510159 A | 4/2007 |
| JP | 2008-51773 A | 3/2008 |
| WO | WO 00/06980 A1 | 2/2000 |

OTHER PUBLICATIONS

Written Opinion of the International Searching Authority issued in PCT/JP2011/070402, dated Dec. 20, 2011.

* cited by examiner

| SCAN POSITION Y | EXCITATION LIGHT WAVELENGTH (nm) | FLUORESCENCE SPECTRUM |
| --- | --- | --- |

FIG. 13

| SCAN POSITION Y | ADDRESS X | EXCITATION LIGHT WAVELENGTH (nm) | FLUORESCENCE WAVELENGTH (nm) | FLUORESCENCE INTENSITY (a.u.) |
|---|---|---|---|---|

FIG. 14

| SCAN POSITION Y | ADDRESS X | EXCITATION LIGHT WAVELENGTH (nm) | FLUORESCENCE WAVELENGTH (nm) | FLUORESCENCE INTENSITY (a.u.) |
|---|---|---|---|---|
| 1 | 1 | 365 | 420 | 200 |
|   |   |     | 440 | 265 |
|   |   |     | 450 | 275 |
|   |   |     | 460 | 260 |
|   |   | 405 | 420 | ... |
|   |   |     | 440 | ... |
|   |   |     | 450 | ... |
|   |   |     | 460 | ... |
| 1 | 2 | ... | ... | ... |
| 1 | 3 | ... | ... | ... |
| ⋮ | ⋮ | ⋮ | ⋮ | ⋮ |

MEASURING DEVICE, MEASURING SYSTEM, MEASURING METHOD, CONTROL PROGRAM, AND RECORDING MEDIUM

TECHNICAL FIELD

The present invention relates to a measuring device, a measuring system, and a measuring method for measuring the intensity of fluorescence that is generated by irradiating a living body with excitation light.

BACKGROUND ART

Recently, with westernization of diets, patients of lifestyle-related diseases are increasing, resulting in serious medical and social problems. At present, in Japan, the number of diabetic patients is 8,000,000, and the number of diabetic patients plus pre-diabetic patients is 20,000,000. The three main complications of diabetes are retinopathy, nephropathy, and neuropathy. Diabetes is also a cause for arteriosclerosis. Furthermore, diabetes may cause heart diseases and brain diseases.

A person develops diabetes in such a manner that improper diets and life styles, secretion from fat cells due to fatness, or oxidative stress decreases the function of pancreas, causing shortage of insulin that controls a blood glucose level or reducing the effect of insulin. Diabetes has symptoms such as frequent urination and increased amount of urination, and increased thirst. However, such symptoms may not enable patients to realize that they develop diabetes, and most patients know their illness when they are subjected to inspection in hospitals etc. This tells why there are so many "silent" diabetic patients.

At the stage where abnormal symptoms resulting from the complications of diabetes are found in hospitals etc., conditions of the disease have advanced too far, making it difficult to completely cure the disease. In particular, many of the complications of diabetes are difficult to cure, and therefore prevention of diabetes is considered as important like many life-style related diseases. For the prevention, early identification and early determination of therapeutic effect are essential, and there are many inspections for diabetes for this purpose.

When a person undergoes oxidative stress in a situation where blood contains abnormal amounts of carbohydrates and lipids therein, the oxidative stress causes reactions of the carbohydrates and the lipids with protein so that AGEs (Advanced Glycation Endproducts) are produced. AGEs are end products produced via non-enzymatic glycosylation reaction of protein (Miallard reaction). AGEs exhibit yellowish brown color, emit fluorescence, and form crosslink by bonding to nearby proteins.

AGEs are considered to be deposited on and infused into blood vessel walls or to interact with macrophage which is a part of an immune system, to thereby release cytokine that is one type of protein and to cause inflammation, resulting in arteriosclerosis.

In the case of diabetes, as the blood glucose level increases, the amount of AGEs increases. Accordingly, by monitoring AGEs, it is possible to identify diabetes at an early stage or to comprehend the progress of diabetes. One example of a method for screening diabetes mellitus by monitoring AGEs is reported in Patent Literature (PTL) 1.

With the reported method, AGEs are monitored by irradiating the skin of a forearm with excitation light, measuring a fluorescence spectrum from the AGEs bound to skin collagen, and comparing the measured fluorescence spectrum with a predetermined model. Thus, AGEs data is obtained in a non-invasive manner.

CITATION LIST

Patent Literature

PTL 1: Japanese Unexamined Patent Application Publication "Translation of PCT Application No. 2007-510159 (published on Apr. 19, 2007)"

PTL 2: Japanese Unexamined Patent Application Publication "Application No. 2010-088070 (filed on Apr. 6, 2010)"

SUMMARY OF INVENTION

Technical Problem

However, the method described in PTL 1 has a problem that, when measurement is repeated plural times, a measurement value varies even with the measurement made on the same examinee in a similar portion, and reliable measurement results are not obtained. The inventors of the present invention have found that such a problem is caused because an irradiation position of the excitation light differs for each measurement.

The above-mentioned problem does not occur only in the measurement of AGEs, and it may likewise occur when any kind of fluorescent substance existing in a subject, e.g., collagen or elastin, is measured in a non-invasive and non-destructive manner.

The present invention has been accomplished with intent to solve the above-mentioned problem, and an object of the present invention is to provide a measuring device, a measuring system, a measuring method, a control program, and a recording medium, which are free from variations in measurement value caused by shift of the irradiation position of the excitation light, and which realize measurement of a fluorescent substance with high accuracy.

Solution to Problem

To solve the above-mentioned problem, the measuring device according to the present invention comprises measurement data obtaining means for obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence, position information obtaining means for obtaining, from a driving mechanism for controlling relative positions of the scanning mechanism and the measurement target, position information indicating an irradiation position where the measurement target is irradiated with the excitation light when the measurement data is obtained, and fluorescence characteristic management means for preparing fluorescence characteristic data including the measurement data obtained by the measurement data obtaining means and the position information obtained by the position information obtaining means.

With such an arrangement, the positional relation between the measurement target and the scanning mechanism (including the excitation light irradiation unit and the light receiving unit) is controlled and grasped by the driving mechanism. Accordingly, when the scanning mechanism performs measurement and obtains the measurement data, the driving mechanism can specify a region in the measurement target where the detection has been performed (i.e., the irradiation position) based on the relative positions of the scanning mechanism and the measurement target at that time.

The measurement data obtaining means of the measuring device obtains the measurement data from the scanning mechanism. On the other hand, the position information obtaining means obtains, as the position information, the information indicating the irradiation position at the time when the measurement data is obtained, from the driving mechanism.

Finally, the fluorescence characteristic management means prepares the fluorescence characteristic data including the measurement data and the position information. In other words, the measurement data and the position information are linked in correspondence relation with each other and are managed as the fluorescence characteristic data.

In the fluorescence characteristic data, the position information and the measurement data are linked in correspondence relation with each other. By looking at the fluorescence characteristic data, therefore, a user can recognize from which position in the measurement target the fluorescence is generated. Thus, even when the measurement data is obtained by changing the relative positions of the scanning mechanism and the measurement target with the driving mechanism, it is possible to always distinctly determine that the obtained measurement data represents the data of the fluorescence generated from which position in the measurement target.

Hitherto, fluorescence has been detected by applying a tip of a fiber or a probe, which emits excitation light, to be placed onto the measurement target. Therefore, the irradiation position is always specified as any one "point" on the measurement target, and one measurement is performed just at one "point".

In contrast, according to the above-described arrangement of the present invention, the measurement (scan) can be performed while the relative positions of the scanning mechanism and the measurement target are moved by the driving mechanism while recognizing those relative positions. It is hence possible to perform multipoint measurement, i.e., measurement with respect to a "plane", by one scan.

Moreover, the measurement data is managed as the fluorescence characteristic data in correspondence to the position information based on the above-described relative positions. Accordingly, the measurement result over the entire "plane" of the measurement target can promptly be output in a batched manner. The measurement result obtained from the entire "plane" can provide more abundant information than that obtained from the "point". For example, a mapping image representing in which region fluorescence intensity is strong at which wavelength can be realized only with the measurement with respect to the "plane".

In the measurement with respect to the "point" using a fiber or a probe as in the related art, it has been required to specify at which "point" the irradiation position is to be set. Accordingly, there has been a problem that the irradiation position varies for each measurement and a measurement value also varies. Furthermore, an angle at which the fiber or the probe is applied to be placed onto the measurement target may also affect the measurement value. Thus, it has been very difficult to repeat the measurement with respect to the "point" under exactly the same conditions.

In contrast, with the above-described arrangement of the present invention, the measurement is performed in a batched manner while a "surface" of the measurement target is scanned. Therefore, specifying the irradiation position in terms of point is no longer required, and the problem of variations in measurement value for each measurement is solved. Moreover, multipoint measurement can be realized in a prompt and simple way.

To solve the above-described problem, a measuring method of the present invention comprises a measurement data obtaining step of obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence, a position information obtaining step of obtaining, from a driving mechanism for controlling relative positions of the scanning mechanism and the measurement target, position information indicating an irradiation position where the measurement target is irradiated with the excitation light when the measurement data is obtained, and a fluorescence characteristic management step of preparing fluorescence characteristic data including the measurement data obtained in the measurement data obtaining step and the position information obtained in the position information obtaining step.

Advantageous Effects of Invention

The measuring device according to the present invention is featured in comprising measurement data obtaining means for obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence, position information obtaining means for obtaining, from a driving mechanism for controlling relative positions of the scanning mechanism and the measurement target, position information indicating an irradiation position where the measurement target is irradiated with the excitation light when the measurement data is obtained, and fluorescence characteristic management means for preparing fluorescence characteristic data including the measurement data obtained by the measurement data obtaining means and the position information obtained by the position information obtaining means.

The measuring method according to the present invention is featured in comprising a measurement data obtaining step of obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence, a position information obtaining step of obtaining, from a driving mechanism for controlling relative positions of the scanning mechanism and the measurement target, position information indicating an irradiation position where the measurement target is irradiated with the excitation light when the measurement data is obtained, and a fluorescence characteristic management step of preparing fluorescence characteristic data including the measurement data obtained in the measurement data obtaining step and the position information obtained in the position information obtaining step.

Thus, the measurement data (e.g., fluorescence characteristics) based on the position information can be visualized. Further advantageous effects can be obtained in that variations in, e.g., the irradiation position and the irradiation angle are eliminated, and that the measurement result of a fluorescent substance can be obtained as two-dimensional information with higher accuracy.

As one example of practical advantageous effects, an AGEs distributed state in blood vessels can be confirmed without employing an image sensing device.

BRIEF DESCRIPTION OF DRAWINGS

FIG. 13 illustrates a data structure of fluorescence characteristic data stored in a fluorescence characteristic data storage unit of a measuring device according to another embodiment of the present invention.

FIG. 14 illustrates a practical example of the fluorescence characteristic data stored in the fluorescence characteristic data storage unit.

DESCRIPTION OF EMBODIMENTS

Embodiment 1

An embodiment of the present invention will be described below with reference to FIGS. 1 to 12.

In the embodiment described below, a measuring system of the present invention measures, as one example, an objective fluorescent substance from a measurement target when a human being is a subject. In this embodiment, the measurement target is, e.g., the forearm of a human being, and the fluorescent substance is, e.g., AGEs. However, the measuring system of the present invention is not limited to such an application, and it can be used to measure fluorescent substances existing at any measurement locations in any substances and any living bodies as subjects.

[Fundamental Construction of Measuring System]

Figure 2:
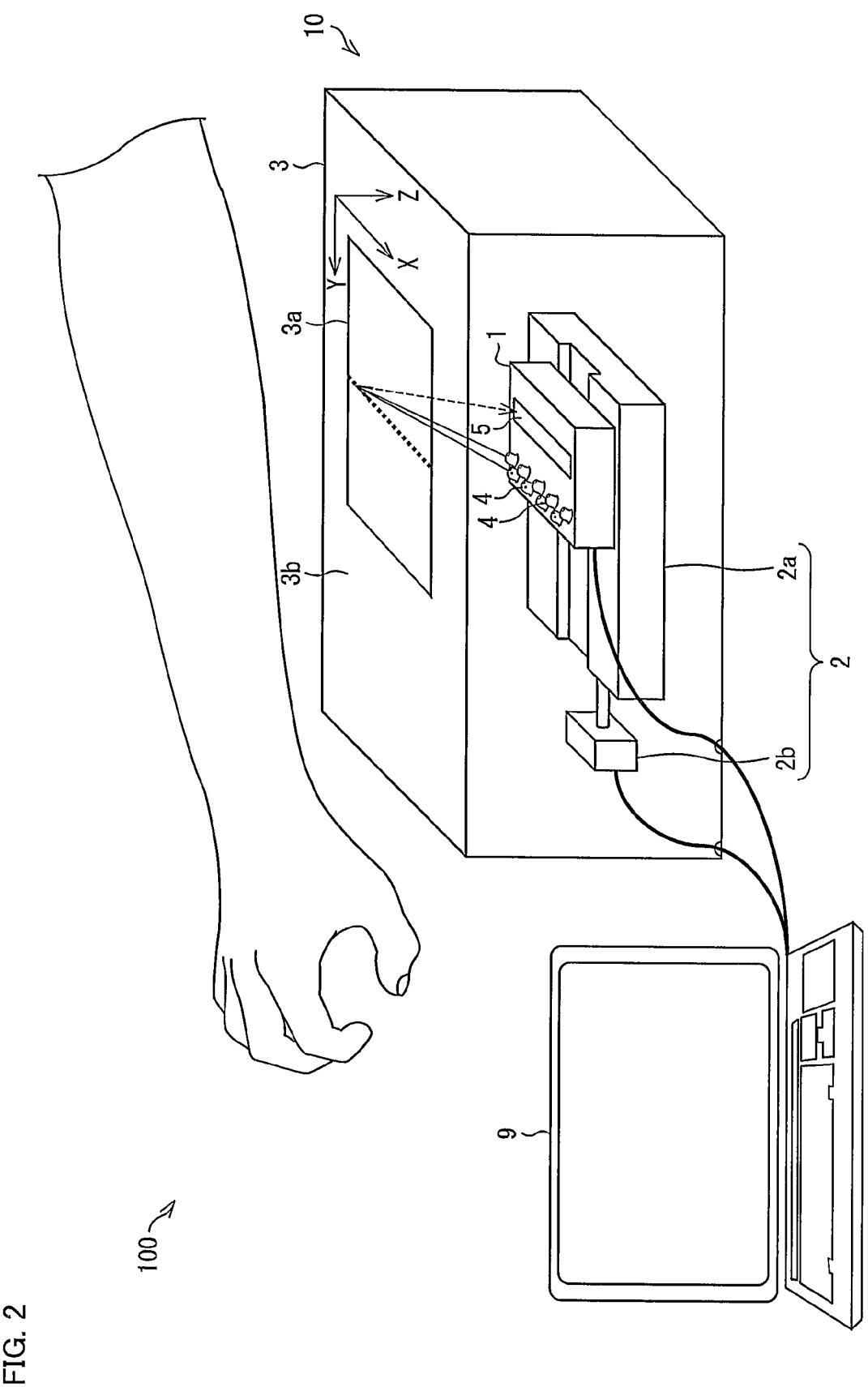
FIG. 2 is a schematic view illustrating a fundamental construction of a measuring system according to the one embodiment of the present invention.

FIG. 2 is a schematic view illustrating a fundamental construction of a measuring system 100 according to the embodiment of the present invention. As illustrated in FIG. 2, the measuring system 100 includes a detecting device 10 and a measuring device 9. The detecting device 10 detects the fluorescent substance from the subject. The measuring device 9 controls various units of the detecting device 10 and performs determination, measurement, etc. of the fluorescent substance based on the detection results obtained by the detecting device 10.

As illustrated in FIG. 2, the detecting device 10 includes a scanning mechanism 1, a driving mechanism 2, and a casing 3 containing both the mechanisms.

The casing 3 contains the scanning mechanism 1 and the driving mechanism 2 therein, and its upper surface provides a place on which the measurement target of the subject is rested. As illustrated in FIG. 2, the casing 3 is constituted by a window portion 3a and a light shielding portion 3b. The window portion 3a is made of quartz. Preferably, it is confirmed that the window portion 3a absorbs no ultraviolet ray. Thus, excitation light having ultraviolet wavelength and emitted from the inside of the casing 3 for irradiation passes through the window portion 3a and reaches the measurement target rested on the window portion 3a. Furthermore, fluorescence radiated from the measurement target enters the casing 3 and reaches the inside of the scanning mechanism 1. The light shielding portion 3b functions to cut off environmental light reaching a fluorescence introducing portion 5 from the out side of the casing 3, and to efficiently obtain the fluorescence, which is generated from the measurement target upon irradiation with the excitation light, in the inside of the scanning mechanism 1. The light shielding portion 3b may be made of plastic, e.g., PP (polypropylene), light shielding polystyrene, polyethylene, or polyethylene terephthalate. Instead of those resins, the light shielding portion 3b may be made of paper, metal, wood or any other suitable material with an aluminum foil attached to an inner side of the container. However, light shielding plastics are practically advantageous in consideration of portability, economic efficiency, and durability.

The scanning mechanism 1 irradiates each measurement target, e.g., an arm, a wrist, an earlobe, a fingertip, a palm, a cheek, of the subject with excitation light and detects fluorescence generated upon the irradiation with the excitation light. The scanning mechanism 1 includes an excitation light source 4 emitting the excitation light to the measurement location, and the fluorescence introducing portion 5 for introducing the fluorescence radiated from the measurement location to the inside of the scanning mechanism 1. As illustrated in FIG. 2, the excitation light (denoted by a solid-line arrow) emitted from the excitation light source 4 reaches the measurement location through the window portion 3a in the upper surface of the casing 3. The measurement location (arm) is in fact held in close contact with the upper surface of the casing 3. Furthermore, the fluorescence (denoted by a dotted-line arrow) radiated from the measurement location is received by the fluorescence introducing portion 5 through the window portion 3a.

A position of the scanning mechanism 1 relative to the measurement target can be changed with operation of the driving mechanism 2. The scanning mechanism 1 successively irradiates the measurement target with the excitation light while the relative position to the measurement target is changed, and further detects, at each relative position, the fluorescence generated from the measurement target at a position under the irradiation with the excitation light. Accordingly, the irradiation position in the measurement target is successively moved with change of the relative position of the scanning mechanism 1 to the measurement target. As a result, the scanning mechanism 1 can obtain optical characteristics of the fluorescence by presenting the irradiation position in the measurement target over a plane instead of a particular one point, i.e., by scanning a plane (that defines a surface of the window portion 3a in the example illustrated in FIG. 2). In other words, a particular irradiation position in the measurement target is no longer required to be taken into consideration in the measurement, and the irradiation position is avoided from varying for each measurement.

More specifically, in this embodiment, the excitation light source 4 of the scanning mechanism 1 is disposed, as illustrated in FIG. 2, to cover (irradiate) a certain region having substantially the same width as that of the window portion 3a in the X-axis direction (e.g., a strip region denoted by a dotted line in the window portion 3a) as the irradiation position. Moreover, the fluorescence introducing portion 5 has substantially the same width as that of the window portion 3a in the X-axis direction, and it is disposed so as to receive almost all rays of the fluorescence radiated through the above-mentioned strip region.

In this embodiment, therefore, the scanning mechanism 1 is able to scan the entire surface of the window portion 3a (i.e., to irradiate the measurement target with the excitation light and to receive the fluorescence radiated therefrom) just by being driven over the window portion 3a in the Y-axis direction. In the following, the irradiation position extending over the window portion 3a along the X-axis and covered by one scan, e.g., the strip region denoted by the dotted line in the window portion 3a in FIG. 2, is called a "scan line". The scan line can be specified by a Y-coordinate in the window portion 3a.

The scanning mechanism 1 includes a detector 8 (details of which will be described below) therein, and it can analyze the received fluorescence to prepare measurement data. The scanning mechanism 1 is connected to the measuring device 9 to be able to communicate with each other in a wired or wireless manner. Thus, the scanning mechanism 1 scans the window portion 3a in units of scan line and then supplies the measurement data of the received fluorescence for each scan line to the measuring device 9.

The driving mechanism 2 drives the scanning mechanism 1 and controls relative positions of the scanning mechanism 1 and the measurement location. In this embodiment, the driving mechanism 2 moves the scanning mechanism 1 to an optional position in the window portion 3a in the Y-axis direction for scanning with an optional scan line on the surface of the window portion 3a.

In more detail, the driving mechanism 2 includes a motor-driven stage 2a and a stage controller 2b. The motor-driven stage 2a includes a plate member (not illustrated) that is movable over a lane (groove). The scanning mechanism 1 is mounted on the plate member and is physically connected thereto. Furthermore, the plate member is electrically connected to the stage controller 2b. Accordingly, the plate member is moved over the lane in accordance with control of the stage controller 2b such that the scanning mechanism 1 can be moved to an optional position in the Y-axis direction.

The stage controller 2b controls the motor-driven stage 2a and adjusts the position of the scanning mechanism 1 in the Y-axis direction. The stage controller 2b is connected to the measuring device 9 to be able to communicate with each other in a wired or wireless manner. While the stage controller 2b may be controlled by the measuring device 9, the stage controller 2b may directly control the motor-driven stage 2a for simplification.

The stage controller 2b holds, in correspondence to a position of the scanning mechanism 1, a Y-coordinate (scan position Yi) of the scan line on the window portion 3a, which scan line is covered by the scanning mechanism 1 when the scanning mechanism 1 is at the relevant position, and it supplies the Y-coordinate to the measuring device 9. As a result, the measuring device 9 can manage, in correspondence to the scan position Yi, the measurement data of the fluorescence received through the fluorescence introducing portion 5 when the scanning mechanism 1 is at a certain position.

The stage controller 2b drives the scanning mechanism 1 at a rate of, e.g., 1 to 25.5 ms per scan line (which corresponds to the fluorescence information processing time of the scanning mechanism 1 per scan line).

[Structure of Scanning Mechanism]

Figure 3:
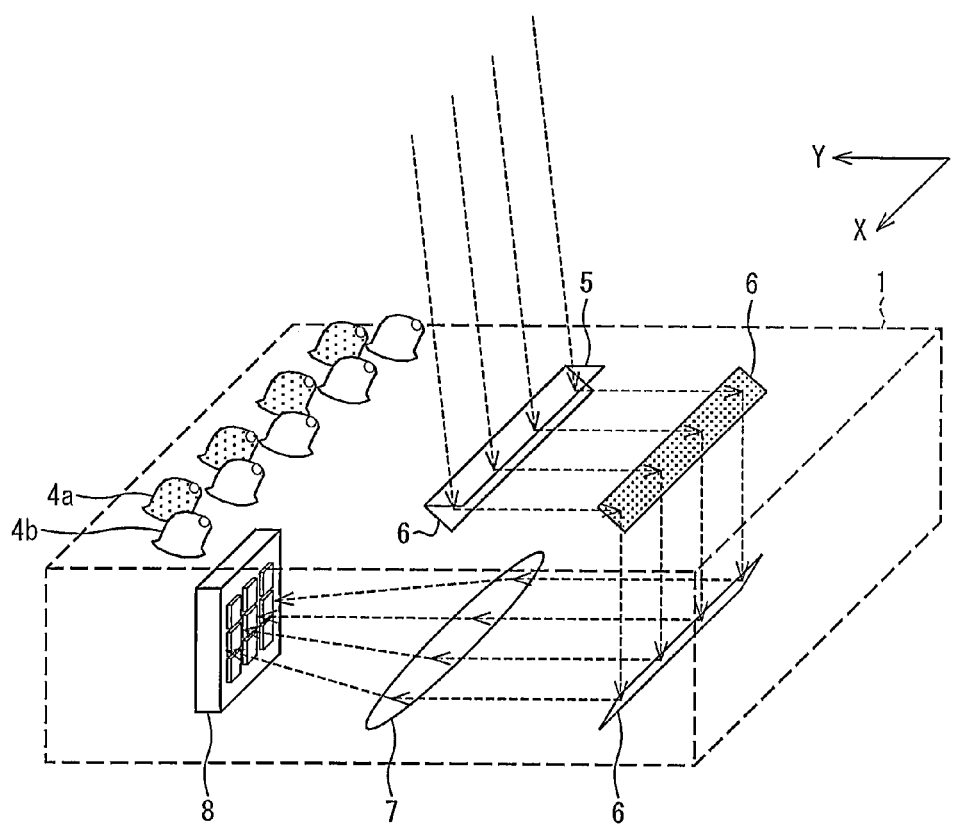
FIG. 3 is a perspective view illustrating, in a seeing-through manner, a fundamental internal structure of a scanning mechanism according to the embodiment of the present invention.
Figure 4:
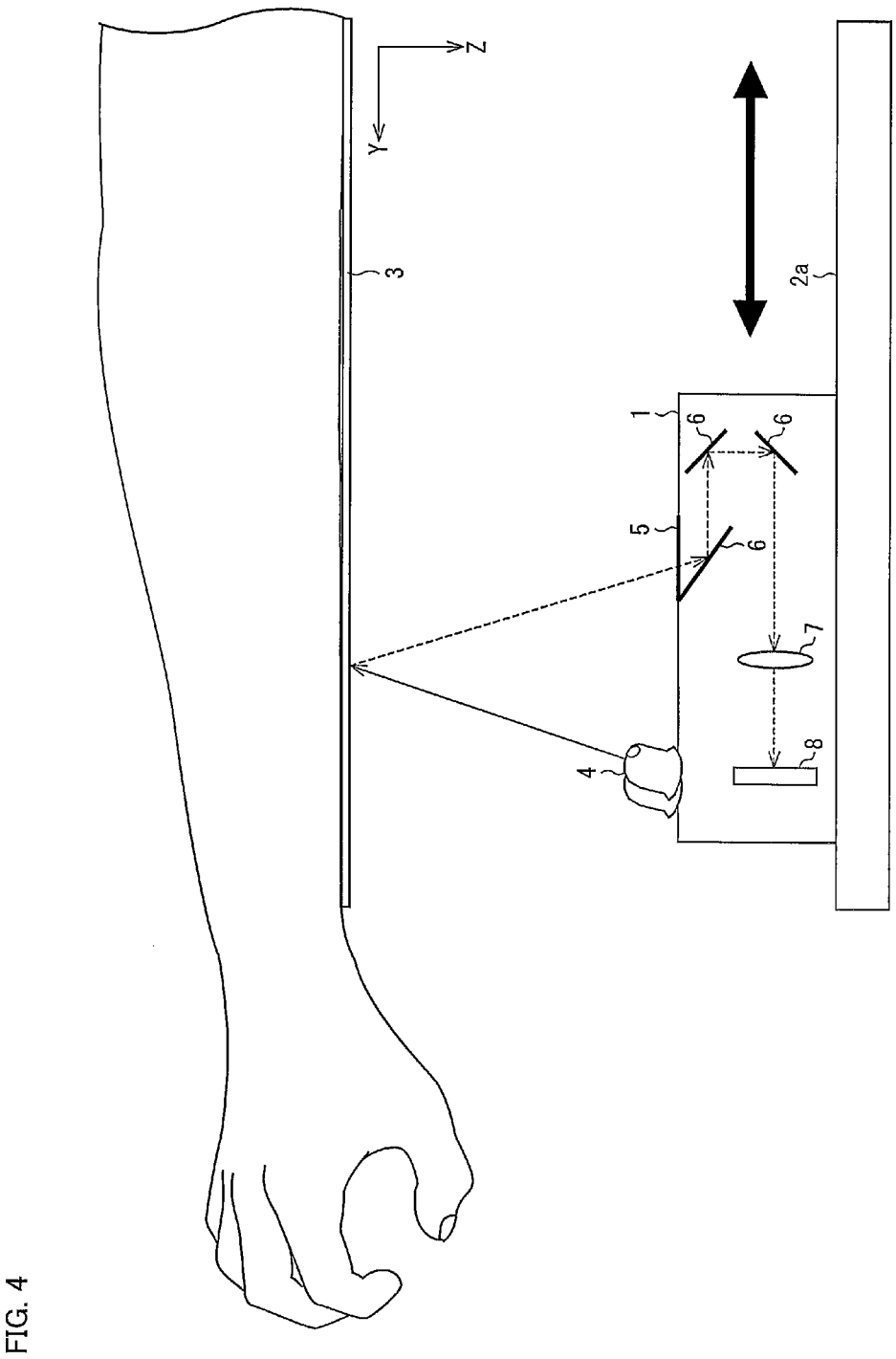
FIG. 4 is a side view illustrating, in a seeing-through manner, the fundamental internal structure of the scanning mechanism.

FIG. 3 is a perspective view illustrating, in a seeing-through manner, a fundamental internal structure of the scanning mechanism 1 according to the embodiment of the present invention. In FIG. 3, for easier visual understanding of the internal structure, the casing of the scanning mechanism 1 is illustrated by dotted lines, and components contained within the scanning mechanism 1 are illustrated by solid lines. FIG. 4 is a side view illustrating, in a seeing-through manner, the fundamental internal structure of the scanning mechanism 1. As illustrated in FIGS. 3 and 4, the scanning mechanism 1 includes the excitation light source 4 and the fluorescence introducing portion 5 on the outer side, and light guiding members 6, a lens 7, and a detector 8 on the inner side. A solid-line arrow in FIGS. 3 and 4 denotes an advancing path of the excitation light emitted from the excitation light source 4, and dotted-line arrows denote advancing paths of the fluorescence received by the detector 8.

The excitation light source 4 is a light emitting device for emitting the excitation light toward the measurement location of the subject that is rested on the window portion 3a. In this embodiment, the excitation light is adapted for detecting the fluorescence generated from AGEs, and it has a wavelength range adapted for measuring the AGEs.

Figure 5:
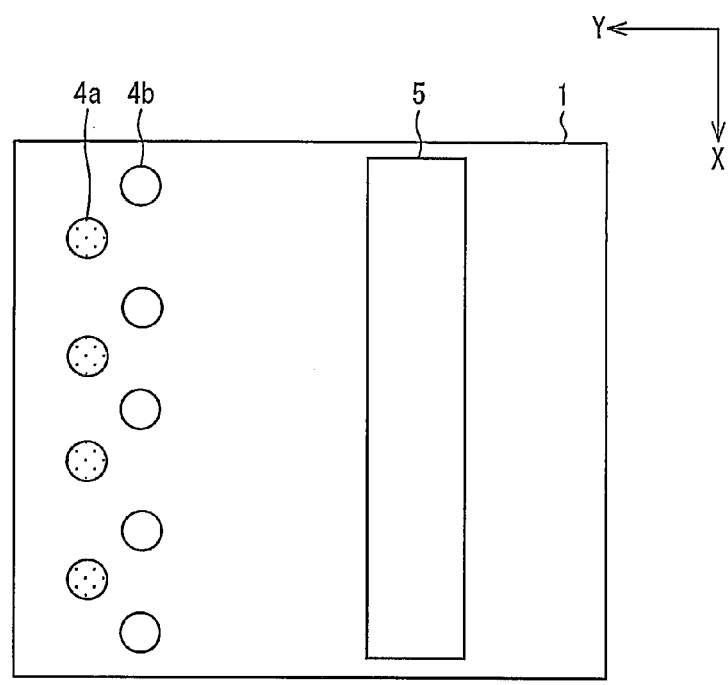
FIG. 5 is a plan view of the scanning mechanism when looking at the scanning mechanism from the side including a window portion.

FIG. 5 is a plan view of the scanning mechanism 1 when looking at the scanning mechanism 1 from the side including the window portion 3a. In this embodiment, as illustrated in FIGS. 3 and 5, the excitation light source 4 is constituted by, for example, an ultraviolet LED 4a having wavelength of 230 to 365 nm and a visible light LED 4b having a wavelength of 405 nm. As illustrated in FIG. 5, the ultraviolet LED 4a (365 nm) and the visible light LED 4b (405 nm) are alternately arranged in a zigzag pattern on the upper surface of the scanning mechanism 1. The excitation light source 4 controls energization of the ultraviolet LED 4a and the visible light LED 4b to be changed over in accordance with control of the measuring device 9. While each of the LEDs used here may have a diameter of about 4.85 mm, for example, the diameter of the LED is not limited to such a value.

By irradiating a particular location (e.g., a blood vessel) of the measurement target with the excitation light having the above-mentioned wavelength, fluorescence is generated from a substance accumulated on a blood vessel wall at the irradiation position. Furthermore, by selectively employing the two types of light sources, the measuring device 9 can specify in more detail properties of the fluorescent substance accumulated on the blood vessel wall. The measuring device 9 analyzes measurement data obtained with the irradiation using the two types of the excitation lights. Moreover, the measuring device 9 recognizes a point at which excitation occurs with the excitation light of 365 nm, but excitation doe not occur with the excitation light of 405 nm, to be a location where the fluorescence attributable to NADH is particularly excited. Thus, the measuring device 9 determines that the relevant location is not a location where AGEs are accumulated. Such an analysis process executed by the measuring device 9 will be described later.

The fluorescence introducing portion 5 introduces the fluorescence, which is radiated from the measurement target and which passes through the window portion 3a, to the inside of the scanning mechanism 1. While the fluorescence introducing portion 5 may be in the form of a simple opening, it may include a slit for increasing wavelength resolution. For example, numerous slits each having a width of 35 to 500 µm may be formed in the fluorescence introducing portion 5 perpendicularly to the X-axis. The provision of the slits enables the fluorescence having entered the scanning mechanism 1 to be efficiently introduced to the detector 8 in corresponding relation to individual photocells thereof, thus consequently increasing the wavelength resolution of the detector 8.

More specifically, when the detector 8 includes photocells in number of 5400/line (two rows for each color of RGB) and the fluorescence introducing portion 5 has a width of 200 mm in its lengthwise direction, it is preferable that the slits each having a width of about 35 µm are formed in the fluorescence introducing portion 5. However, the slit width is not limited such a value, and it may be determined as appropriate depending on specifications of the detector 8 and occurrence situations of noise (i.e., variations in a signal level). The slits may be formed at intervals in one-to-one (1:1) relation to all the photocells of the detector 8. Instead of the slits, pin holes ($\phi$10 to 50 µm) may be formed in the fluorescence introducing portion 5.

The light guiding members 6 serve to efficiently guide, to the detector 8, the fluorescence having entered the scanning mechanism 1 via the fluorescence introducing portion 5, and each light guiding member 6 is constituted by a mirror. Layout positions of the light guiding members 6 are not limited to those illustrated in FIGS. 3 and 4, and they are designed as appropriate depending on the direction of the fluorescence incident upon the fluorescence introducing portion 5 and the positional relation with respect to the detector 8. In this embodiment, as illustrated in FIGS. 3 and 4, three light guiding members 6 are disposed in such a layout as allowing the fluorescence to be introduced perpendicularly to a light receiving surface of the detector 8.

The lens 7 is a converging lens for introducing the fluorescence, which is to be received by the detector 8, to the detector 8 with higher accuracy.

The detector 8 receives the fluorescence, which is generated from the measurement location upon irradiation with the excitation light, through the above-described arrangement, and analyzes the received fluorescence, thereby measuring the wavelength of the fluorescence and the intensity of the fluorescence per wavelength. In other words, the detector 8 measures at what level of intensity the fluorescence has been detected at which wavelength. The detector 8 is constituted by, e.g., a spectrometer. Specifications of the detector 8 are not limited to particular ones on condition that the detector 8 can detect light in an objective wavelength band. The detector 8 detects the fluorescence by employing image sensing elements in the form of, e.g., a CCD (Charge Coupled Device) or a CMOS (Complementary Metal-Oxide-Semiconductor), and analyzes detected fluorescence signals.

The fluorescence introduced to the detector 8 through the fluorescence introducing portion 5 is separated for each address that is set in correspondence to the X-axis coordinate of the window portion 3a. In the detector 8, for example, the intensity of the fluorescence is converted to a numerical value for each address of a CCD pixel. Stated another way, the fluorescence corresponding to one scan line specified by the Y-coordinate of the window portion 3a can further be specified by the X-coordinate.

The detector 8 transmits measurement data, which is obtained by converting the analyzed result to an electric signal, to the measuring device 9 via a communication cable or a wireless communication means. The detector 8 successively transmits the electric signal (measurement data) to the measuring device 9 for each scan position (or for each scan position and for each address). The signal successively transmitted from the detector 8 for each scan position may be provided as a signal represented on a time-serial timing chart.

In this embodiment, as illustrated in FIG. 2, the measuring device 9 may control the detector 8 via a communication cable. In accordance with control of the measuring device 9, the detector 8 produces, as the measurement data, a fluorescence spectrum obtained by averaging all fluorescence characteristics at a particular scan position (Y-coordinate), or produces, as the measurement data, a fluorescence spectrum for each scan position (Y-coordinate) and for each address (X-coordinate). Additionally, in accordance with control of the measuring device 9, the detector 8 performs setting of an integrated time for the detection, taking-in of data, etc.

Figures 6, 7:
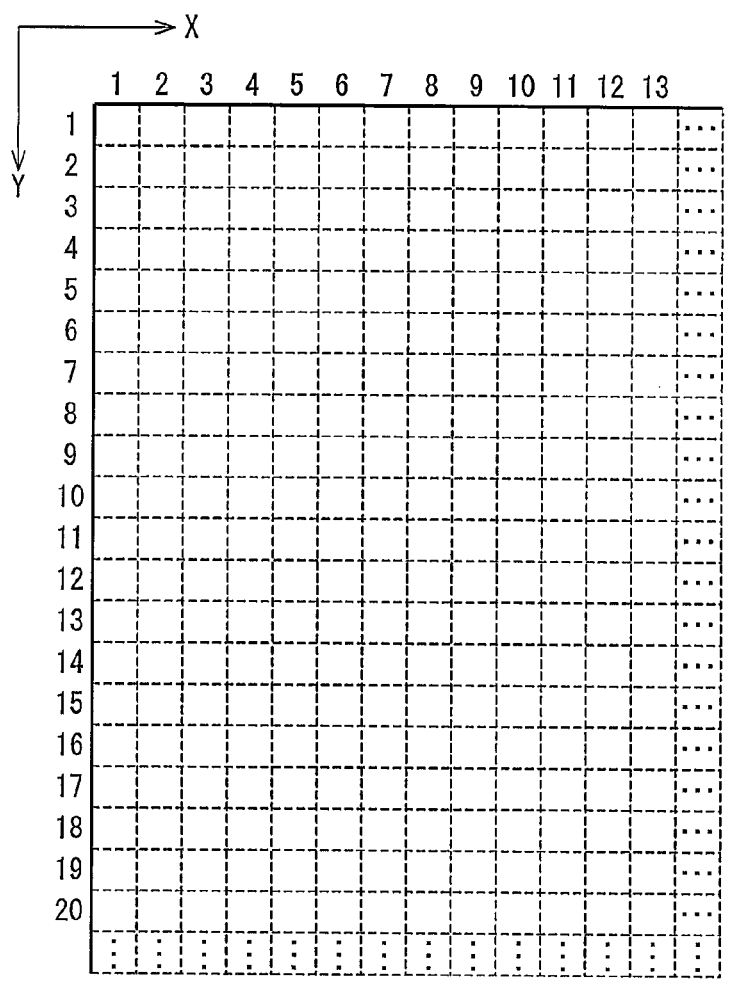
FIG. 6 illustrates, in an enlarged scale, addresses (X-coordinates) and scan positions (Y-coordinates) in a part of a window portion.
FIG. 7 illustrates a data structure of fluorescence characteristic data stored in a fluorescence characteristic data storage unit of the measuring device according to the one embodiment of the present invention.

FIG. 6 illustrates, in an enlarged scale, addresses (X-coordinates) and scan positions (Y-coordinates) in a part of the window portion 3a. It is to be noted that coordinate information illustrated in FIG. 6 is logical information and does not imply physical division of the window portion 3a.

In this Embodiment 1, the detector 8 supplies the measurement data obtained for each scan position (Y-coordinate), illustrated in FIG. 6, to the measuring device 9. The measurement data output from the detector 8 is linked in correspondence relation with the scan position, which is output from the driving mechanism 2, by the measuring device 9.

In the detector 8, the fluorescence signal representing optical characteristics of the fluorescence is converted to the electric signal by, e.g., a CCD for visualization and is supplied as the measurement data to the measuring device 9. In the measuring device 9, the measurement data is then linked in correspondence relation with the position information (scan position here) in the window portion 3a. Therefore, the measuring device 9 can present, to a user, both the blood vessel position in the measurement target (arm) of the subject and the measurement result that enables the user to confirm the state of accumulated AGEs, by executing an analysis of the measurement data and image processing based the position information.

While the size and the specifications of the scanning mechanism 1 are not limited to particular ones, the scanning mechanism 1 may be constituted using, e.g., a flat scanner head capable of reading data over a width of 100 mm with resolution of 600 dpi.

The configuration and the operation of the measuring device 9 to measure an objective fluorescent substance and to visualize the measurement result by employing the measurement data transmitted from the detector 8 in this Embodiment 1 will be described in detail below.

It is be noted that, in another embodiment, the detector 8 supplies measurement data obtained for each scan position (Y-coordinate) and for each address (X-coordinate), illustrated in FIG. 6, to the measuring device 9. In that case, the detector 8 supplies, to the measuring device 9, the measurement data per address at a certain scan position in correspondence to the address (X-coordinate). As a result, each measurement data output from the detector 8 is managed in the measuring device 9 in correspondence to the scan position and the address. Operations of individual devices when the detector 8 outputs the measurement data for each scan position (Y-coordinate) and for each address (X-coordinate) will be described in detail below in Embodiment 2.

[Configuration of Measuring Device]

Figure 1:
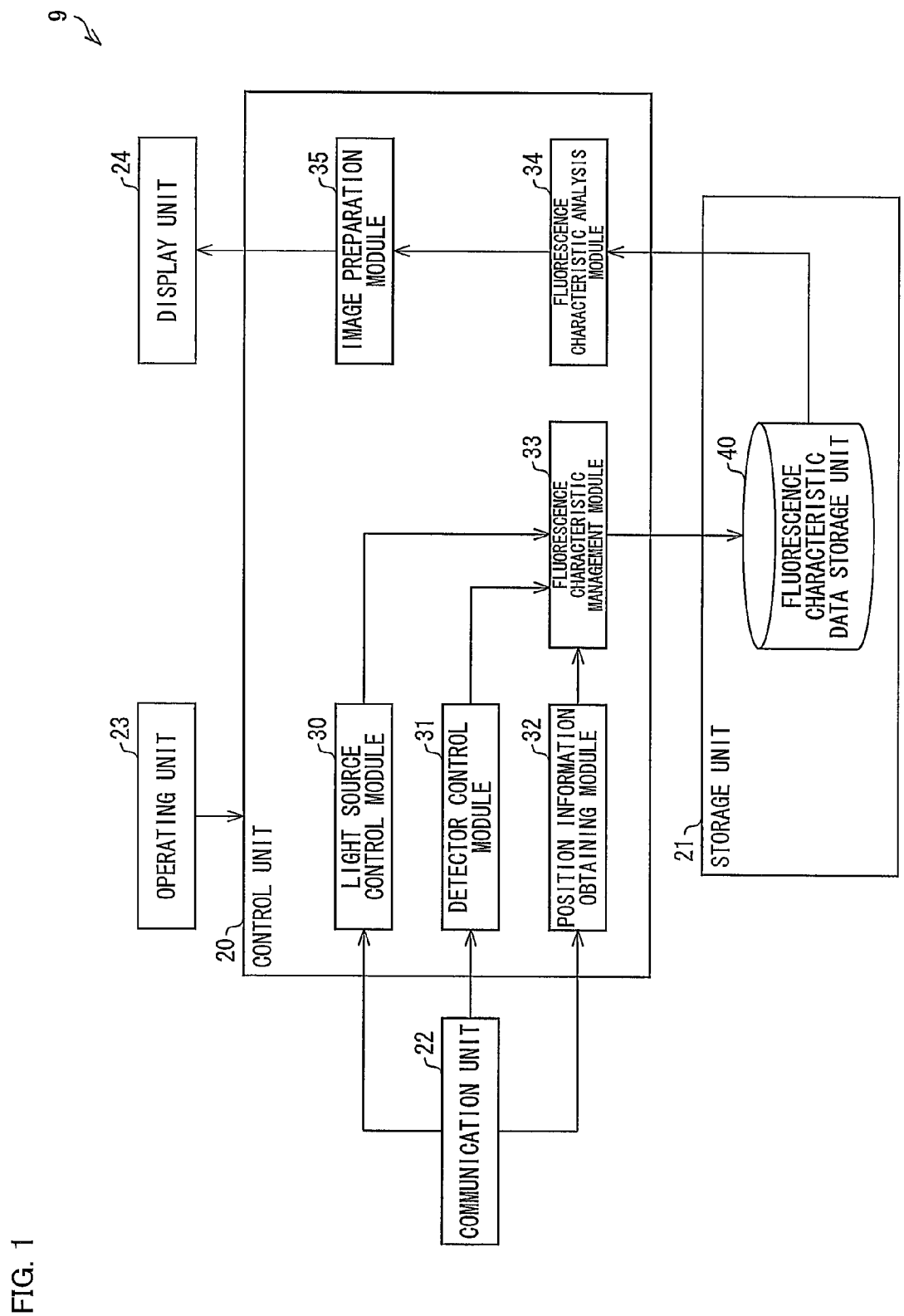
FIG. 1 is a block diagram illustrating a fundamental configuration of a measuring device according to one embodiment of the present invention.

FIG. 1 is a block diagram illustrating a fundamental configuration of a measuring device 9 according to the embodiment of the present invention.

As illustrated in FIG. 1, the measuring device 9 according to this embodiment includes a control unit 20, a storage unit 21, a communication unit 22, an operating unit 23, and a display unit 24.

The communication unit 22 executes communication with an external device via a communication network. The communication unit 22 transmits and receives data to and from various components of the detecting device 10, i.e., the excitation light source 4, the detector 8, and the stage controller 2b in the scanning mechanism 1 via communication cables, for example. Thus, the communication unit 22 transmits control signals to the above-described various components and receives the measurement data and conditions (such as the wavelength of the excitation light and the scan position) of the performed measurement from those various components. The communication unit 22 may include the wireless communicating function. Such a feature is advantageous in that, because data can be transmitted to and received from the various components of the detecting device 10 without using communication cables, the degree of freedom in design of the measuring system 100 increases.

The operating unit 23 is manipulated by the user to input an instruction signal to the measuring device 9. The operating unit 23 is constituted by proper one or more of input devices including, e.g., a keyboard, a mouse, buttons (such as arrow keys, an Enter key, and character input keys), a touch panel, a touch sensor, and a touch pen, as well as a voice input unit and a voice recognition unit.

The display unit 24 displays the measurement result of the fluorescence substance, the measurement result being managed by the measuring device 9, or displays, as a GUI (Graphical User Interface) screen, an operating screen on which the user operates the measuring device 9. The display unit 24 is constituted, for example, by a display device such as an LCD (liquid crystal display).

Additionally, the measuring device 9 includes a temporary storage unit (not illustrated). The temporary storage unit is the so-called working memory to temporarily store data used in computations, computation results, etc. during various types of processing executed by the measuring device 9. The temporary storage unit is constituted by, e.g., a RAM.

The storage unit 21 stores (1) control programs executed by the control unit 20, (2) an OS program executed by the control unit 20, (3) application programs with which the control unit 20 executes various functions of the measuring device 9, and (4) various data read out when the control unit 20 executes the application programs. In particular, the storage unit 21 stores various programs and data, which are read out when executing the fluorescent substance measuring process to be performed by the measuring device 9. More specifically, the storage unit 21 includes a fluorescence characteristic data storage unit 40.

The control unit 20 controls various components of the measuring device 9 in a supervising manner. The control unit 20 includes, as function blocks, a light source control module 30, a detector control module 31, a position information obtaining module 32, a fluorescence characteristic management module 33, a fluorescence characteristic analysis module 34, and an image preparation module 35.

The above-mentioned function blocks of the control unit 20 can be realized with a CPU (central processing unit) reading respective programs stored in a storage device (storage unit 21), which is constituted by, e.g., a ROM (read only memory) or an NVRAM (non-volatile random access memory), to be loaded into a not-illustrated temporary storage unit (RAM: random access memory) or the like, and then executing those programs.

The light source control module 30 of the control unit 20 controls the excitation light source 4 of the scanning mechanism 1. In this embodiment, the excitation light source 4 includes two types of light sources, i.e., the ultraviolet LED 4a and the visible light LED 4b, which are disposed in the scanning mechanism 1. Accordingly, the light source control module 30 controls turning-on and -off of those two types of LEDs at proper timing. For example, when the measurement intended to measure the fluorescent substance "AGEs" is instructed from the user, individual measurement data obtained with irradiations using both the types of LEDs are required to more accurately visualize the AGEs detected position. Therefore, when the measurement object is instructed by the user as the measurement of "AGEs", the light source control module 30 makes control to turn on each of the ultraviolet LED 4a and the visible light LED 4b in an optional sequence. Alternatively, the light source control module 30 changes over the turned-on LED at proper timing.

The detector control module 31 controls the detector 8 and obtains the necessary measurement data from the detector 8. For example, the detector control module 31 is realized with the CPU reading and executing VisualSpectra2.1Sr that is stored as detector control software in the storage unit 21.

The position information obtaining module 32 controls the driving mechanism 2, especially the stage controller 2b, and obtains, from the stage controller 2b, the position information when the scanning mechanism 1 performs a scan. As a result, the measurement data output from the detector 8 can be linked in correspondence relation with the position information. In this embodiment, because the scanning mechanism 1 performs a scan for each scan line specified with the Y-coordinate, the position information obtaining module 32 obtains the scan position Y from the stage controller 2b.

The fluorescence characteristic management module 33 produces fluorescence characteristic data from the result of the measurement that is carried out using the various components of the detecting device 10. Furthermore, the fluorescence characteristic management module 33 stores the prepared fluorescence characteristic data in the fluorescence characteristic data storage unit 40 and manages the stored data. More specifically, the fluorescence characteristic management module 33 links the measurement data (fluorescence spectrum), which is obtained from the detector 8 through the detector control module 31, in correspondence relation with the irradiation position in the measurement target, i.e., with the position information of the window portion 3a (i.e., the scan position Y in this embodiment), at the time when the relevant measurement data is obtained. Information regarding the correspondence between the measurement data and the position information is stored as fluorescence characteristic data in the fluorescence characteristic data storage unit 40.

FIG. 7 illustrates a data structure of the fluorescence characteristic data stored in the fluorescence characteristic data storage unit 40 in the embodiment.

As illustrated in FIG. 7, the fluorescence characteristic data in this embodiment has a data structure in which at least the measurement data (fluorescence spectrum) and the position information (scan position Y) are linked in correspondence relation with each other. The correspondence information may further include a measurement condition (wavelength of the excitation light). In this embodiment, the measurement is preformed twice at the same scan position in some cases by employing the two types of excitation light sources 4. In such a case, the fluorescence characteristic management module 33 obtains, from the light source control module 30, the measurement condition (wavelength of the excitation light) at the time when the measurement data is obtained. Then, the fluorescence characteristic management module 33 stores, as the fluorescence characteristic data, the relevant measurement data, the relevant position information, and the relevant wavelength of the excitation light in the linked form in the fluorescence characteristic data storage unit 40.

The scan position Y is used to specify the scan position, which is irradiated with the excitation light, based on a logical Y-coordinate value in the window portion 3a, as illustrated in FIG. 6.

Figure 8:
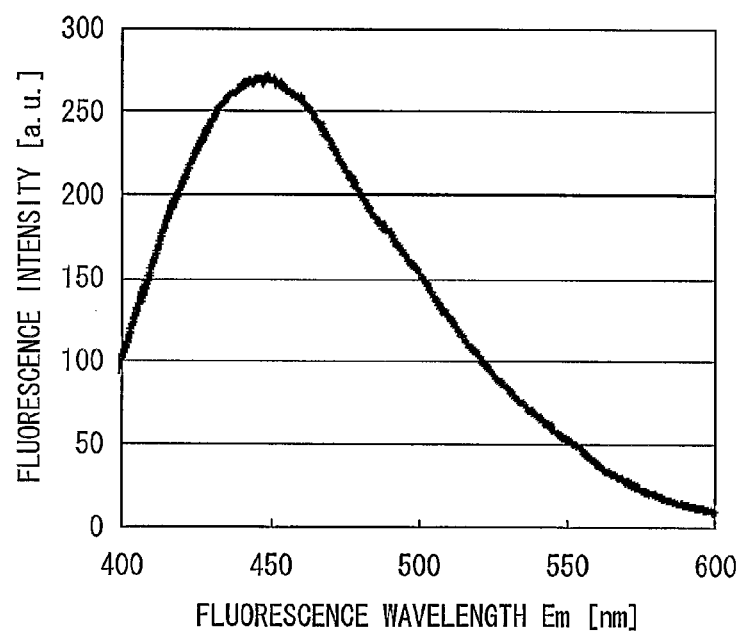
FIG. 8 is a graph depicting a fluorescence spectrum of AGEs when the AGEs are irradiated with excitation light at a wavelength of 365 nm.

The fluorescence spectrum is information that is contained in the measurement data obtained from the detector 8. The fluorescence spectrum represents at what level of intensity the fluorescence has been detected at which wavelength. As illustrated in FIG. 8, for example, the fluorescence spectrum can be visualized in the form of a two-dimensional graph where the horizontal axis represents the fluorescence wavelength and the vertical axis represents the fluorescence intensity. The fluorescence characteristic management module 33 may further extract another feature variable from the fluorescence spectrum and may store the extracted feature variable in correspondence to the position information instead of the fluorescence spectrum or in addition to the fluorescence spectrum. The feature variable is, for example, fluorescence intensity at a particular fluorescence wavelength, peak fluorescence intensity, a fluorescence wavelength at the peak intensity, a half value width, an average value of fluorescence intensity.

The fluorescence characteristic analysis module 34 compiles and analyzes the fluorescence characteristic data stored in the fluorescence characteristic data storage unit 40 for each item of the position information, and further produces map information for visualizing the measurement result. More specifically, the measurement data obtained as the fluorescence characteristic data or the feature variable extracted from the measurement data is plotted on a two- or three-dimensional map in agreement with the position information. The map information plotting the measurement data for each position is supplied from the fluorescence characteristic analysis module 34 to the image preparation module 35.

The image preparation module 35 prepares a visualization image, which is to be displayed on the display unit, based on the map information (information plotting the measurement data for each item of the position information) produced by the fluorescence characteristic analysis module 34. For example, the image preparation module 35 prepares a three-dimensional graph based on the map information, and additionally plots values, points, lines, etc. on the graph. Moreover, the image preparation module 35 depicts a graph in a color-coded manner and adds necessary information to the graph.

Figure 9:
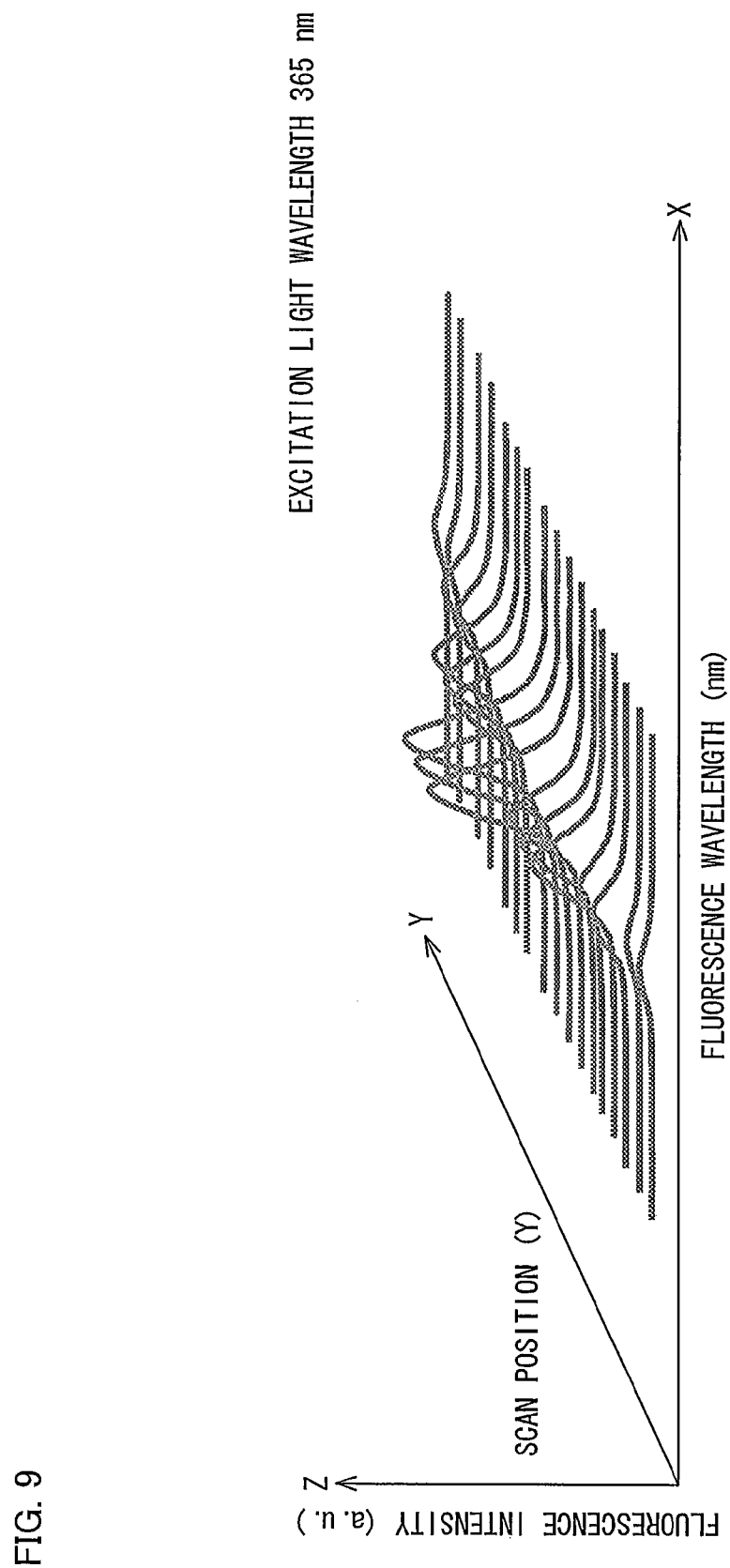
FIG. 9 is a graph depicting one example of a visualization image prepared by a fluorescence characteristic analysis module and an image preparation module of the measuring device according to the one embodiment of the present invention.
Figure 10:
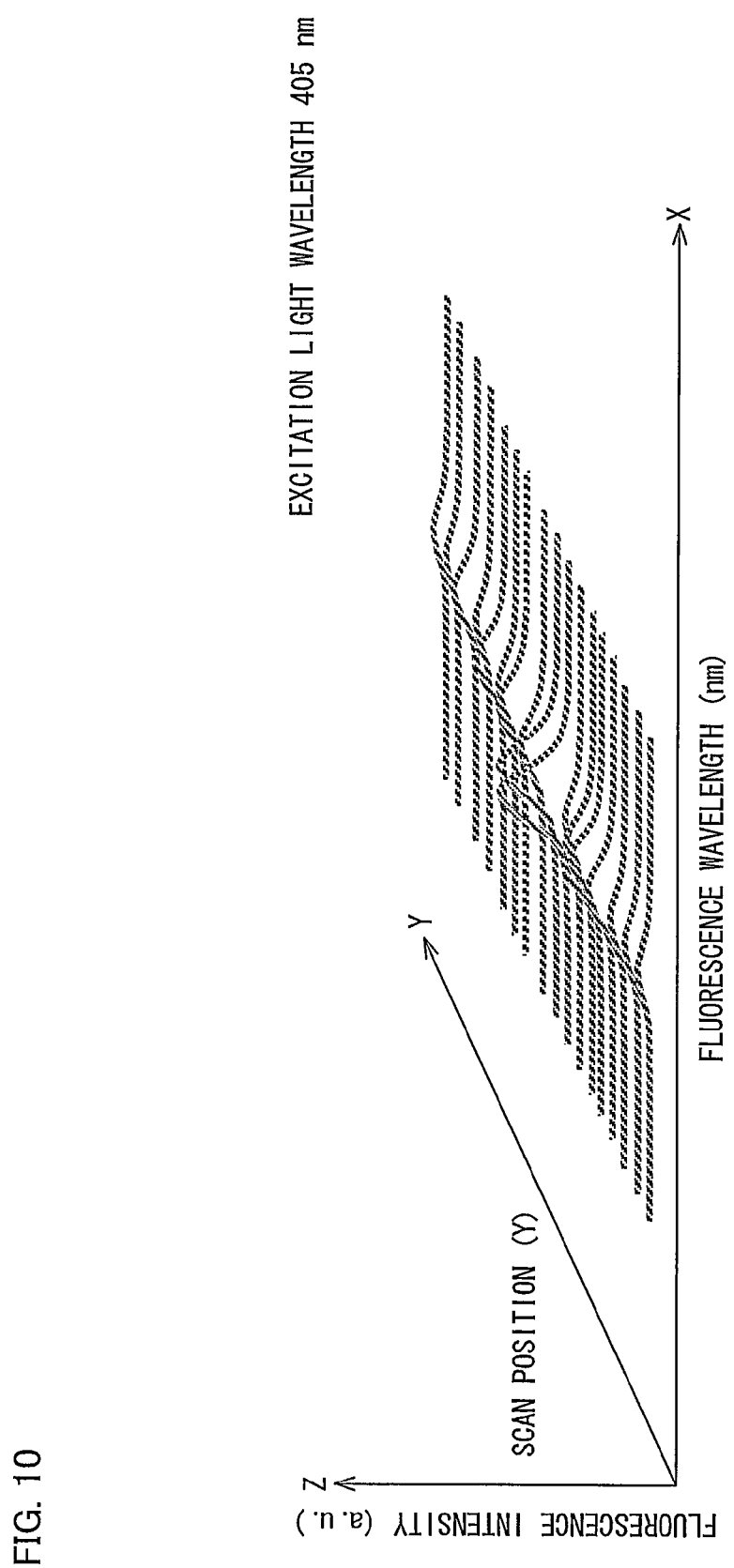
FIG. 10 is a graph depicting one example of the visualization image prepared by the fluorescence characteristic analysis module and the image preparation module of the measuring device according to the one embodiment of the present invention.

FIGS. 9 and 10 are each a graph depicting one example of a visualization image for the measurement result, the image being prepared by the fluorescence characteristic analysis module 34 and the image preparation module 35.

In this embodiment, the visualization image is formed, for example, by plotting the fluorescence spectrum for each scan position on a three-dimensional graph where the X-axis represents the fluorescence wavelength, the Z-axis represents the fluorescence intensity, and the Y-axis represents the scan position. The three-dimensional graph, illustrated in FIG. 9, depicts a set of fluorescence spectra when the measurement target is irradiated with the excitation light of 365 nm by employing the ultraviolet LED 4a. The three-dimensional graph, illustrated in FIG. 10, depicts a set of fluorescence spectra when the measurement target is irradiated with the excitation light of 405 nm by employing the visible light LED 4b.

As seen from the examples illustrated in FIGS. 9 and 10, the fluorescence intensity at a certain fluorescence wavelength is noticeably high at a certain scan position. It is confirmed that, when a fluorescence substance exists at a detection position, the fluorescence intensity is increased in comparison with that at a position where the fluorescence substance does not exist. By looking at the above-mentioned three-dimensional graph, therefore, it is possible to recognize the fact that the fluorescent substance exists in larger amount at the relevant scan position.

With the visualization image displayed on the display unit 24 as described above, the user can recognize at which scan position the fluorescent substance is detected in larger amount. In addition, the user can perform more detailed measurement by focusing on the relevant scan position, or can observe the progress with the lapse of time.

[Measurement Flow]

Figure 11:
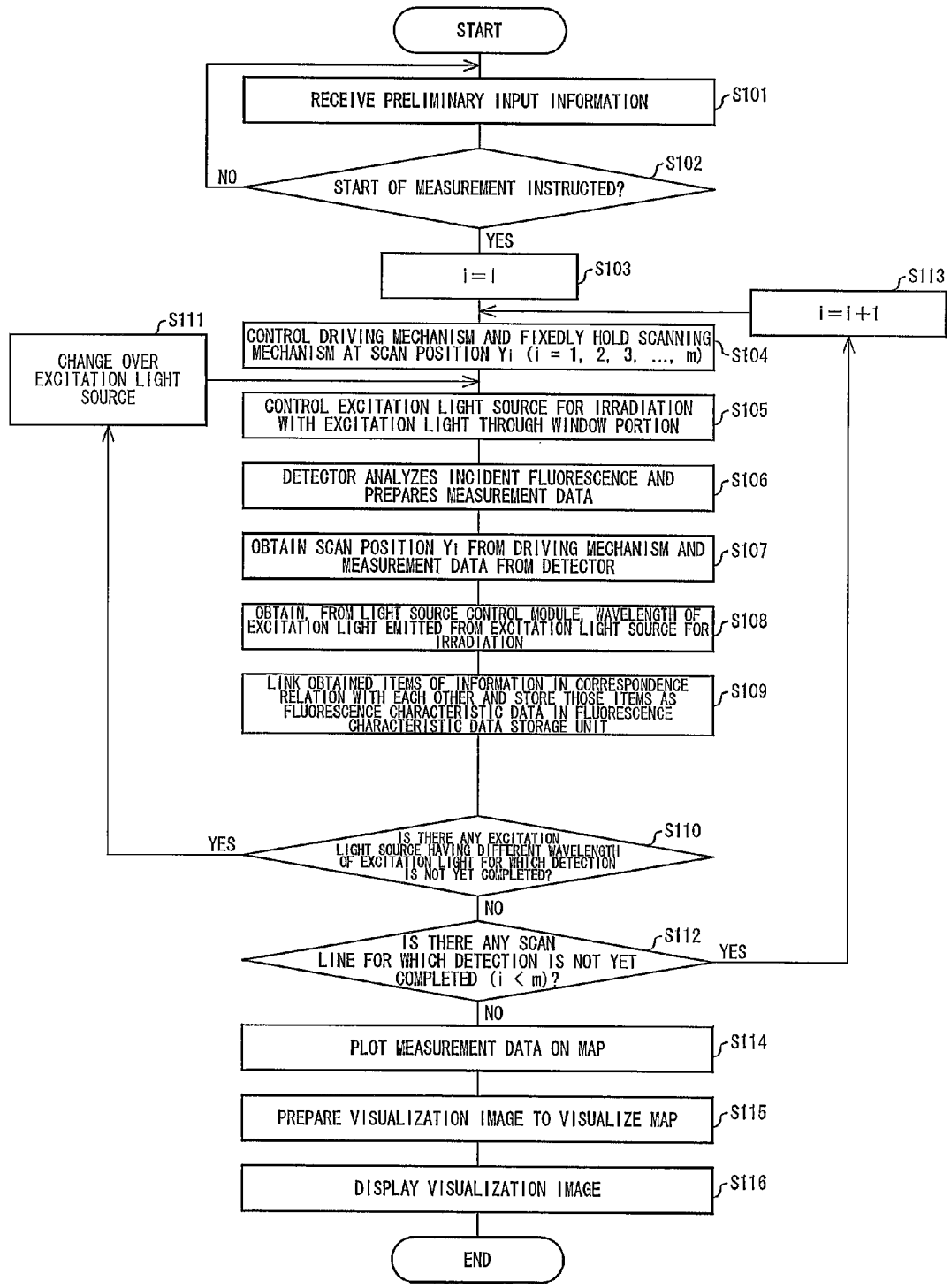
FIG. 11 is a flowchart illustrating flow of a fluorescent substance measuring process executed by various devices of the measuring system according to the one embodiment of the present invention.

FIG. 11 is a flowchart illustrating flow of a fluorescent substance measuring process executed by various devices of the measuring system 100 according to this embodiment.

As illustrated in FIG. 11, the measuring device 9 may first receive, via the operating unit 23, preliminary input information that is to be input from the user in advance, such as measurement conditions, measurement object, subject information, and information regarding the measurement location (S101). In this embodiment, for example, various measurement conditions for "examining the abundance of a fluorescent substance existing in the forearm of a human being" are input.

If a signal instructing the start of measurement is input via the operating unit 23 (YES in S102), the measuring device 9 controls the various components of the detecting device 10 to start a process of measuring the fluorescent substance in the measurement target that is rested on the window portion 3a.

First, the position information obtaining module 32 initializes the scan position Yi (i=1, 2, 3, . . . , m) (S103). Then, the position information obtaining module 32 controls the driving mechanism 2 and fixedly holds the scanning mechanism 1 at the scan position Yi (S104). When a scan is performed for the first time in the relevant measurement process, the scanning mechanism 1 is moved to the first scan position.

Then, the light source control module 30 controls the excitation light source 4 for irradiation with the excitation light through the window portion 3a (S105). The excitation light reaches the measurement target (forearm) through the window portion 3a, and fluorescence radiated from the forearm enters the detector 8 through the fluorescence introducing portion 5 and the various components within the scanning mechanism 1. The detector 8 in the scanning mechanism 1 analyzes the incident fluorescence and prepares measurement data (fluorescence spectrum here) (S106).

The position information obtaining module 32 of the measuring device 9 obtains, from the stage controller 2b, the scan position Yi corresponding to the current position of the scanning mechanism 1. The detector control module 31 obtains the prepared fluorescence spectrum from the detector 8 (S107).

Then, the fluorescence characteristic management module 33 obtains the scan position Yi and the fluorescence spectrum from the position information obtaining module 32 and the detector control module 31, respectively. Moreover, the fluorescence characteristic management module 33 obtains, from the light source control module 30, the wavelength (e.g., 365 nm or 405 nm) of each excitation light used for the irradiation in the relevant measurement (S108).

After linking the "scan position Yi", the "excitation light wavelength", and the "fluorescence spectrum" in correspondence relation with one another, which are obtained from the relevant modules, the fluorescence characteristic management module 33 stores them as fluorescence characteristic data in the fluorescence characteristic data storage unit 40 (S109).

If it is determined that the scan is to be performed at a different excitation wavelength in the same scan position Yi (YES in S110), the light source control module 30 changes over the excitation light source 4 (S111). For example, when the scan with the ultraviolet LED 4a is completed and another scan with the visible light LED 4b is to be performed subsequently, the light source control module 30 turns off the ultraviolet LED 4a and turns on the visible light LED 4b. After the light source has been changed over, the scanning mechanism 1 repeats the processes of S105 and S106, while the various components of the measuring device 9 repeat the processes of S107 to S109.

On the other hand, if the scans at all necessary excitation wavelengths in the same scan position Yi are completed in S110 (NO in S110), the position information obtaining module 32 determines whether the detection has been completed for all the scan positions (scan lines), or any scan line not yet subjected to the detection remains (S112).

If there remains a scan line for which the scan is not yet completed (YES in S112), the position information obtaining module 32 controls the driving mechanism 2 to advance the scan position Yi by one step (S113) and to move the scanning mechanism 1 to the next scan position (S104). Thereafter, the processes of S105 to S109, S110 and S111 are repeated in the same procedures as those described above. The fluorescence spectrum for each scan position and for each excitation wavelength is then stored in the fluorescence characteristic data storage unit 40.

On the other hand, if the scan is completed for all the scan lines (NO in S112), the fluorescence characteristic analysis module 34 plots the fluorescence spectrum on a map based on the fluorescence characteristic data stored in the fluorescence characteristic data storage unit 40, thereby preparing map information (S114).

In accordance with the map information prepared by the fluorescence characteristic analysis module 34, the image preparation module 35 prepares a visualization image to display the map information as a graph or a table on the display unit 24 (S115). Finally, the display unit 24 displays the visualization image (S116), which has been prepared by the image preparation module 35.

With the method described above, for example, the visualization images illustrated in FIGS. 9 and 10 are displayed on the display unit 24. From those images, the user can recognize at which scan position the fluorescent substance is detected in larger amount. Furthermore, the user can perform more detailed measurement by focusing on the relevant scan position, or can observe the progress with the lapse of time.

[Modification]

As described above, since the scanning mechanism 1 includes the two types of excitation light sources 4 having different wavelengths, two fluorescence spectra can be obtained with respect to the same scan position. The fluorescence characteristic analysis module 34 of the measuring device 9 in this embodiment can analyze those two fluorescence spectra from a comprehensive point of view, and can perform more detailed measurement of the fluorescent substance.

In S114 of FIG. 11, the fluorescence characteristic analysis module 34 compares the fluorescence spectrum obtained at the excitation light wavelength of 365 nm with the fluorescence spectrum obtained at the excitation light wavelength of 405 nm. Those fluorescence spectra are stored in the fluorescence characteristic data storage unit 40 in correspondence to the same scan position. The fluorescence characteristic analysis module 34 executes the above-mentioned comparison for each scan position. Furthermore, the fluorescence characteristic analysis module 34 specifies the scan position where a reduction of the fluorescence intensity has been confirmed at a predetermined reduction rate (although the fluorescence intensity is not reduced down to 0) with the changing-over of the excitation light wavelength from 365 nm to 405 nm. Then, the fluorescence characteristic analysis module 34 assigns information (in the form of, e.g., a value, a mark or a flag), indicating that an AGEs-derived substance is contained, to the fluorescence characteristic data obtained at the scan position where a reduction of the fluorescence intensity at a rate of about predetermined % has been confirmed, thereby reflecting such information on the map information.

The above-mentioned reduction rate of the fluorescence intensity can be controlled by adjusting respective irradiation intensities of the excitation light source of 365 nm and the excitation light source of 405 nm. For example, the irradiation intensities of those excitation light sources can be set such that the reduction rate of the fluorescence intensity is obtained at about 45% for the AGEs-derived substance with the changing-over of the excitation light wavelength from 365 nm to 405 nm. In that case, the fluorescence characteristic analysis module 34 specifies the scan position where the reduction of the fluorescence intensity at a rate of about 45% (although the fluorescence intensity is not reduced down to 0) has been confirmed as a result of executing the above-described comparison.

The image preparation module 35 prepares the three-dimensional graphs, illustrated in FIGS. 9 and 10, based on the above-described map information. In addition to preparing the graphs, the image preparation module 35 prepares a visualization image for the fluorescence spectrum in which the scan position assigned with a flag indicating the AGEs-derived substance is displayed in a different color or highlighted to make the relevant scan position more noticeable than other scan positions.

Figure 12:
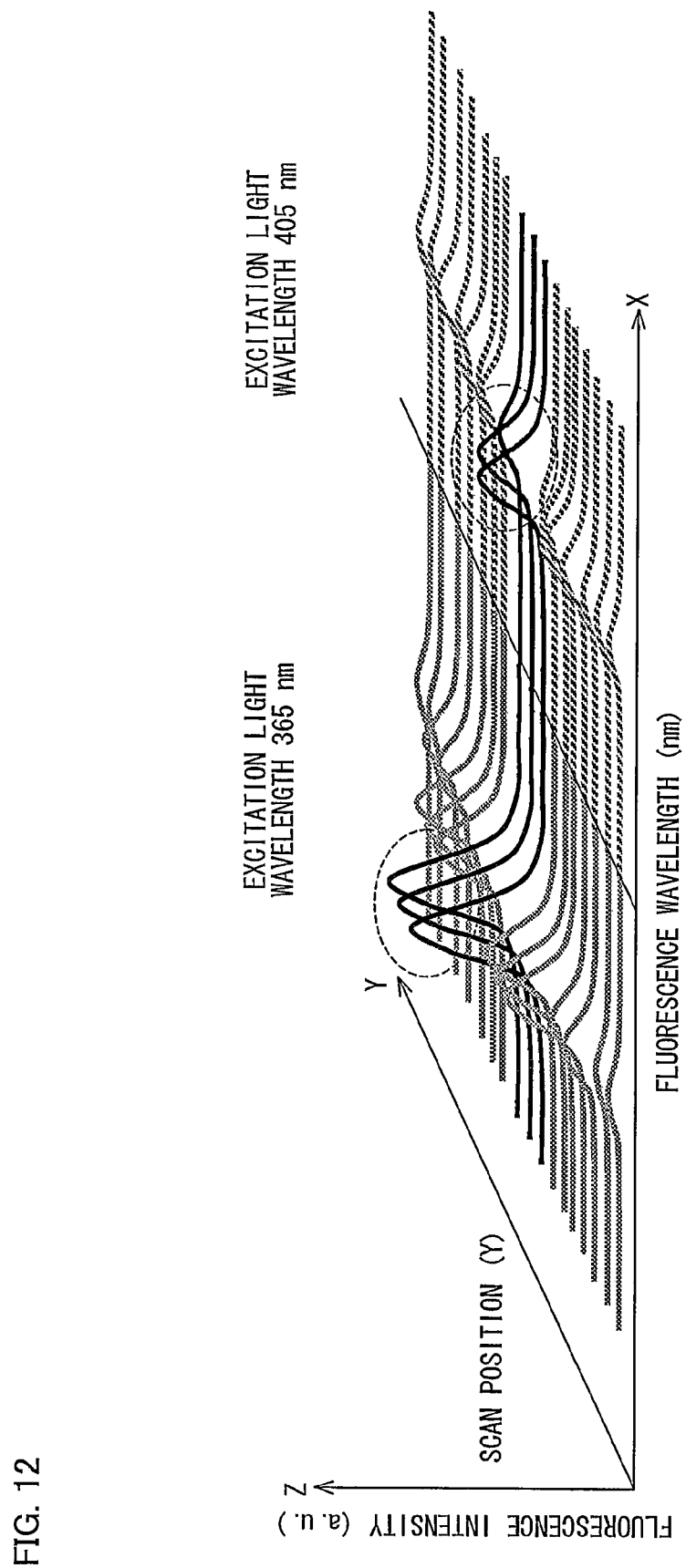
FIG. 12 is a graph depicting a practical example of the visualization image in which the fluorescence spectrum is highlighted at a scan position where a flag indicating an AGEs-derived substance is set.

FIG. 12 is a graph depicting a practical example of the visualization image in which the fluorescence spectrum is highlighted at a scan position where a flag indicating the AGEs-derived substance is set.

As seen from FIG. 12, the fluorescence spectrum is highlighted in a different color at the scan positions where the reduction of the fluorescence intensity at a rate of about 45% appears with the changing-over of the excitation light wavelength from 365 nm to 405 nm.

As a result, the user can visually confirm the scan position where, particularly, the AGEs-derived fluorescent substance among various fluorescent substances exists.

By comparing the fluorescence spectrum obtained at the excitation light wavelength of 365 nm and the fluorescence spectrum obtained at the excitation light wavelength of 405 nm as described above, AGEs, i.e., the fluorescent substance of the measurement object, and reduced nicotinamide adenine dinucleotide (NADH), i.e., a fluorescent molecule existing in the living body as a background, can be measured separately from each other.

Comparing the case excited with the excitation light of 365 nm and the case excited with the excitation light of 405 nm, AGEs exhibit the reduction of the fluorescence intensity at a rate of about 45% (the fluorescence can be detected although the fluorescence intensity is reduced) with the changing-over of the excitation light to the longer wavelength. In contrast, NADH usually considerably absorbs an ultraviolet ray of 340 nm, and fluorescence generated from NADH is hardly detected on the same conditions when it is excited with the excitation light of 405 nm. AGEs and NADH can be identified separately based on such a great difference in the reduction rate of the fluorescence intensity between them.

Thus, the intensity of the fluorescence attributable to AGEs can be specified by detecting how the fluorescence intensity is changed with the changing-over of the excitation light wavelength. As a result, the AGEs and other background substances can be separated from each other.

When the above-described separate identification is performed, two types of visualization images can be obtained (as depicted in FIG. 12) with one measurement by employing the scanning mechanism 1 and the driving mechanism 2 of the present invention and executing scans while different light sources (e.g., 365 nm and 405 nm) are changed over. The scan position where AGEs exist can more accurately be specified by comparing those two types of visualization images with each other.

Embodiment 2

Another embodiment of the present invention will be described below with reference to FIGS. 13 to 20. It is to be noted that, for convenience of explanation, components having the same functions as those of the components described in Embodiment 1 with reference to the drawings are denoted by the same symbols and descriptions of those components are omitted.

In the following, this embodiment is described regarding the configuration and the operation of a measuring device 9 for preparing a visualization image based on fluorescence characteristic data that is obtained for each scan position Y and for each address X.

In this embodiment, various components of a scanning mechanism 1 operate such that fluorescence received for one scan line through a fluorescence introducing portion 5 is introduced to a detector 8 discretely for each address specified by an X-coordinate in a window portion 3a. A light receiving portion of the detector 8 receives the fluorescence per address on an X-axis for one scan line, analyzes the fluorescence for each address Xi, and outputs measurement data. The address may be set such that one address is assigned to one pixel of an image sensing element of the detector 8, or that one address is assigned to each group of several pixels. Assuming here i of the address Xi to be i=1, 2, 3, . . . , n, the detector 8 supplies a number n of measurement data for one scan line to the measuring device 9.

A detector control module 31 of the measuring device 9 obtains the number n of measurement data for each scan line (scan position Yi) in correspondence to respective addresses. The number n of measurement data are made in correspondence to the addresses in one-to-one relation. Accordingly, a fluorescence characteristic management module 33 stores, in a fluorescence characteristic data storage unit 40, the "scan position Y", the "address X", and the "measurement data (fluorescence spectrum)" in correspondence to one another. Information of the address X may be supplied from a stage controller 2b of a driving mechanism 2. The stage controller 2b is capable of monitoring the operation of the scanning mechanism 1 and supplying position information, including the "scan position Y" and the "address X", to the measuring device 9 in synchronism with the operation of supplying the measurement data by the scanning mechanism 1 (detector 8) in sequence for each address.

There is a possibility that, if the fluorescence spectra are stored for all of the scanned coordinates, a data volume would become too large and memory capacity would be insufficient. In consideration of such a point, in this embodiment, the fluorescence characteristic management module 33 extracts a necessary feature variable from the fluorescence spectrum depending on the measurement object, and stores only the extracted feature variable in correspondence to the position information (including the scan position and the address). The measurement object is, for example, determination of shapes of blood vessels, detection of AGEs, and measurement of the amount of skin collagen. In this embodiment, the feature variable is, for example, "fluorescence intensity at a particular fluorescence wavelength", "peak intensity", "average fluorescence intensity", and "fluorescence wavelength at peak", which are extracted from the fluorescence spectrum.

FIG. 13 illustrates a data structure of fluorescence characteristic data stored in the fluorescence characteristic data storage unit 40 in this embodiment.

As illustrated in FIG. 13, the fluorescence characteristic data in this embodiment has a data structure in which the "fluorescence wavelength" and the "fluorescence intensity" are linked in correspondence relation with the "scan position Y", the "address X", and the "excitation light wavelength".

The "fluorescence wavelength" and the "fluorescence intensity" are practical examples of the feature variable extracted from the fluorescence spectrum by the fluorescence characteristic management module 33, and they represent the intensity of the analyzed fluorescence at a certain fluorescence wavelength. For example, the fluorescence characteristic data including the "fluorescence wavelength: 420 nm" and the "fluorescence intensity: 200 (au)" in correspondence to each other indicates the fact that the fluorescence radiated from the relevant position has optical characteristics of exhibiting the fluorescence intensity of 200 (au) at the fluorescence wavelength of 420 nm. Identification and quantitative assay of the objective fluorescent substance existing in the subject can be realized by analyzing such fluorescence characteristics and evaluating them in various ways.

FIG. 14 illustrates a practical example of the fluorescence characteristic data stored in the fluorescence characteristic data storage unit 40. It is to be noted that the fluorescence characteristic data illustrated in FIG. 14 is one example and is not to be construed as limiting the present invention.

In this embodiment, as in Embodiment 1, scans are performed using two types of excitation light sources 4 having different wavelengths (i.e., an ultraviolet LED 4a and a visible light LED 4b). Furthermore, in this embodiment, the fluorescence characteristic management module 33 extracts the fluorescence intensity from the fluorescence spectrum at least at the fluorescence wavelengths of "420 nm" and "460 nm" for the purpose of distinctively visualizing blood vessels and AGEs in the forearm of a human being. In addition, the fluorescence intensity at the fluorescence wavelengths of "440 nm" and "450 nm" may preliminarily be extracted to increase measurement accuracy.

Thus, as illustrated in FIG. 14, the fluorescence characteristic management module 33 stores a value of the "fluorescence intensity" extracted at each of the particular "fluorescence wavelengths (420, 440, 450, 460 nm)" in correspondence to the "scan position Y", the "address X", and the "excitation light wavelength".

As described above, the fluorescence characteristic management module 33 can manage the fluorescence characteristic data, including the above-mentioned feature variables, in the fluorescence characteristic data storage unit 40 for each point that is specified by the X- and Y-coordinates in the window portion 3a.

Next, the fluorescence characteristic analysis module 34 compiles and analyzes the fluorescence characteristic data stored in the fluorescence characteristic data storage unit 40, to thereby prepare map information for visualizing the measurement result.

In this embodiment, the fluorescence characteristic analysis module 34 plots the feature variable for each of the X- and Y-coordinates on a two-dimensional map where an X-axis represents the address and the Y-axis represents the scan position. Here, as one example, the fluorescence characteristic analysis module 34 sorts the fluorescence intensity at the fluorescence wavelength of 460 nm into, e.g., four classes in advance depending on a value of the fluorescence intensity. The four classes are, for example, as follows:

Class 1: fluorescence intensity is less than ** (=no fluorescent substance)

Class 2: fluorescence intensity is not less than ** and less than xx (=small amount of fluorescent substance)

Class 3: fluorescence intensity is not less than xx and less than ○○ (=large amount of fluorescent substance)

Class 4: fluorescence intensity is not less than ○○ (=very large amount of fluorescent substance)

Then, the fluorescence characteristic analysis module 34 plots the classes, which have been determined for all coordinates, on a two-dimensional table such that (X,Y)= (1,1) belongs to the class 1, (X,Y)=(2,1) belongs to the class 1, . . . , (X,Y)=(1,2) belongs to the class 1, . . . , and (X,Y)= (n,m) belongs to the class 3. The fluorescence characteristic analysis module 34 supplies two-dimensional map information, prepared as described above, to an image preparation module 35.

The image preparation module 35 prepares a two-dimensional visualization image based on the two-dimensional map information supplied from the fluorescence characteristic analysis module 34.

Figure 15:
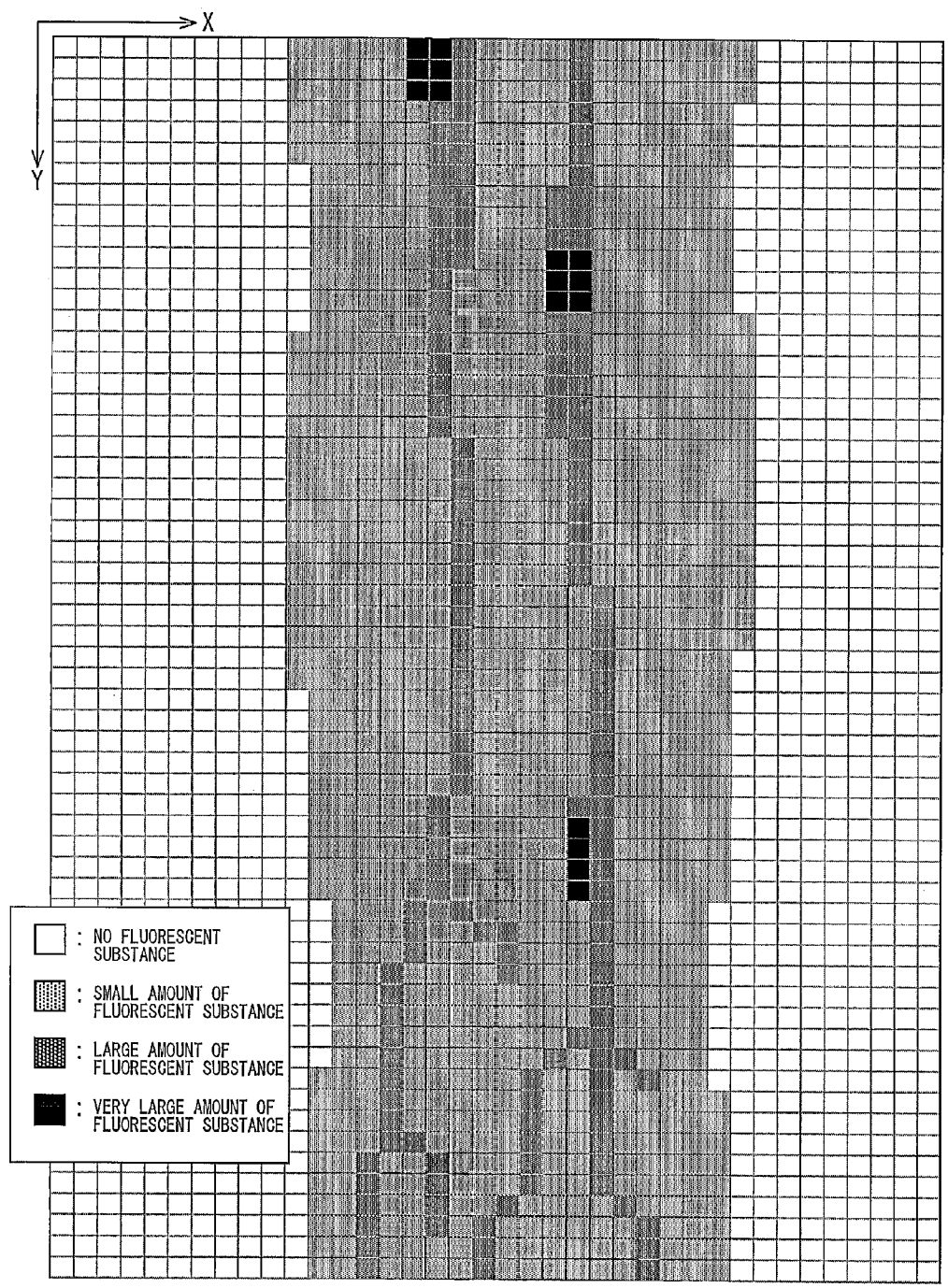
FIG. 15 is a plot depicting a practical example of a visualization image prepared by a fluorescence characteristic analysis module and an image preparation module of the measuring device according to the other embodiment of the present invention.

FIG. 15 is a plot depicting a practical example of the visualization image prepared by the image preparation module 35 in this embodiment.

In this embodiment, as illustrated in FIG. 15, the image preparation module 35 visualizes, e.g., a two-dimensional table made up of the number n of cells in the X-coordinate× the number m of cells in the Y-coordinate, the table corresponding to the above-described two-dimensional map information, and represents those cells in different colors depending on respective designated classes.

With such a visualization image displayed on the display unit 24, the user can visually confirm a distribution of amount of the fluorescent substance in the measurement target.

From experiments, it is confirmed that, because blood vessels exist at a detection position in, e.g., an arm, a wrist, an earlobe, a fingertip, a palm, and a cheek, the fluorescence intensity is increased in comparison with that at a position where no blood vessels exist. Accordingly, as illustrated in FIG. 15, shapes of blood vessels in the measurement target can be visualized by visualizing the fluorescence intensity in correspondence to the position information. In the visualization image illustrated in FIG. 15, for example, the cells corresponding to the class representing "large amount of fluorescent substance" indicate the shapes of the blood vessels with a high probability. Furthermore, it is thought that AGEs accumulated on blood vessel walls exhibit a higher level of fluorescence intensity than fluorescent substances flowing through the blood vessels. Hence, the cells corresponding to the class representing "very large amount of fluorescent substance" indicate the AGEs accumulated positions with a high probability.

According to the measuring system 100 of the present invention, as described above, it is possible to visualize blood vessels and to specify the AGEs accumulated positions by employing only the mechanisms that are essential to measure the fluorescent substance, without needing an additional mechanism to visualize the blood vessels.

The above-described advantages of the present invention will be more apparent from comparison with PTL 2 discussed below.

As a technique for solving the problem caused in the above-described PTL 1, PTL 2 discloses a measuring system including a mechanism for visualizing a measurement location (blood vessel). The visualizing mechanism disclosed in PTL 2 includes a blood-vessel visualizing light source for visualizing the measurement location (blood vessel, etc.), and a camera unit for taking an image of a measurement target illuminated with the blood-vessel visualizing light source. With such an arrangement, the user can visually confirm the measurement location, i.e., the position to be irradiated with excitation light, and hence can adjust the irradiation position of the excitation light to be held constant. As a result, the problem causing a variation in the irradiation position for each measurement can be solved.

However, the arrangement of PTL 2 requires other complicated components for visualizing the measurement location, such as the visualizing light source and the camera unit, in addition to the mechanism (including an excitation light source and a fluorescence detector) necessary for measurement of the fluorescent substance. Therefore, the measuring system is inevitably expensive and complex in configuration. Moreover, because image data taken by the camera unit is processed for visualization of the blood vessel, a high processing load is imposed on the measuring device.

In contrast, according to the measuring system 100 of the present invention, the detecting device 10 performs the detection on the measurement location with respect to a plane instead of a point, and manages the fluorescence spectrum, which is obtained from the plane, in correspondence to each coordinate position on the relevant plane. Therefore, the measurement result can be presented to the user in the form of a two-dimensional visualization image together with the position information. In the two-dimensional visualization image, a representation manner can be changed depending on various different fluorescence characteristics for each of various fluorescent substances. For example, by differentiating a blood vessel and a skin region including no blood vessels depending on whether the fluorescent substance contained in the blood vessel exists or not, and by changing the representation manner between the blood vessel and the skin region, the shape of the blood vessel can also be visualized in addition to the measurement of the objective fluorescent substance.

Thus, it is no longer required to take into account variations in the position (point) to be irradiated with the excitation light and to execute a process for visualizing the blood vessel as a preliminary stage prior to the measurement. As a matter of course, additional components for visualizing the blood vessel are also no longer required.

[Measurement Flow]

Figure 16:
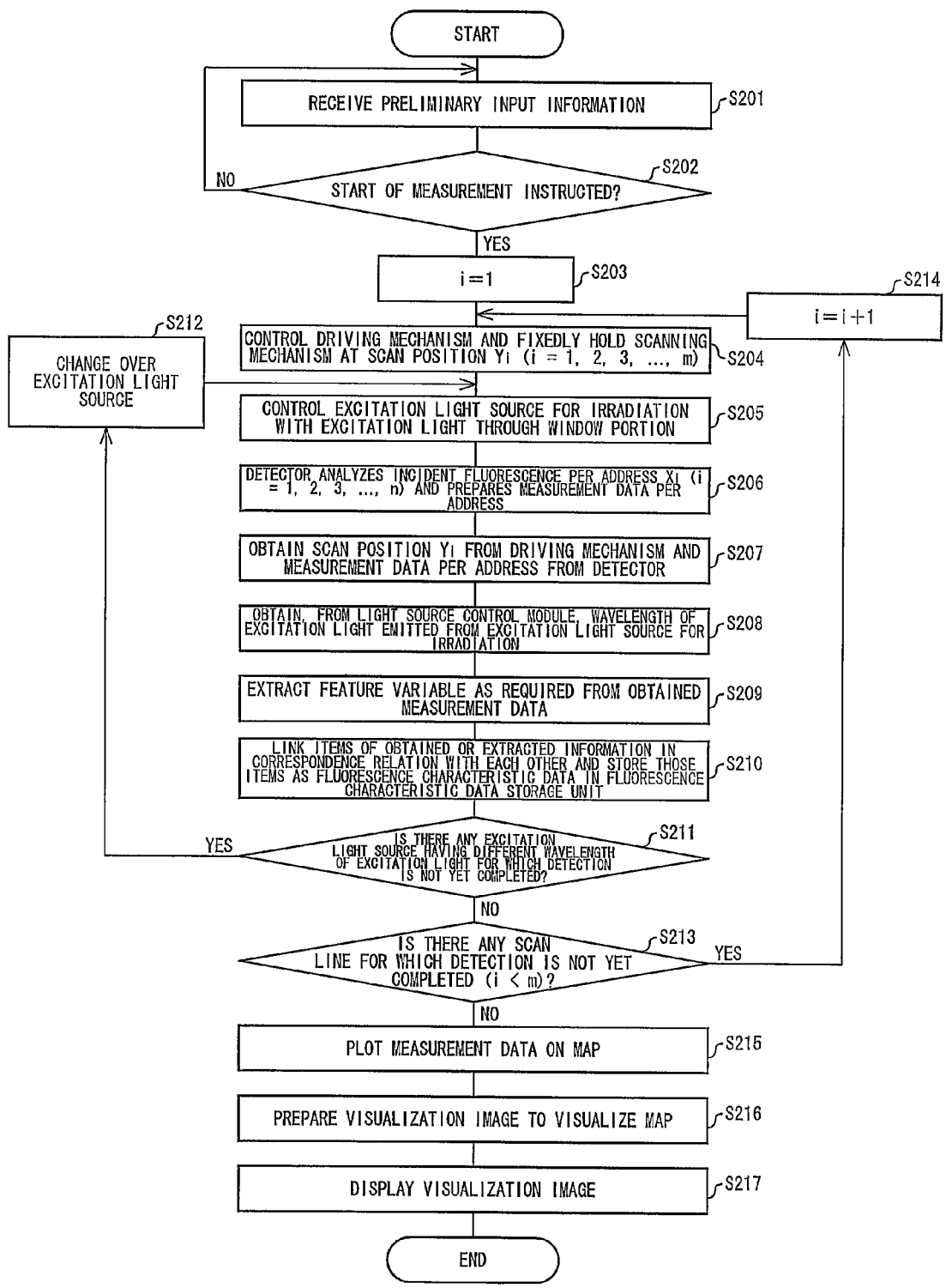
FIG. 16 is a flowchart illustrating flow of a fluorescent substance measuring process executed by various devices of a measuring system according to the other embodiment of the present invention.

FIG. 16 is a flowchart illustrating flow of a fluorescent substance measuring process executed by various devices of the measuring system 100 according to this embodiment.

Processes of S201 to S205 illustrated in FIG. 16 are executed in a similar manner to those of S101 to S105, respectively, described above with reference to FIG. 11.

Thereafter, in this embodiment, the detector 8 receives the fluorescence per address for one scan line, analyzes the fluorescence per address Xi (i=1, 2, 3, . . . , n), and prepares measurement data (S206).

The position information obtaining module 32 obtains, from the stage controller 2b, the scan position Yi corresponding to the current position of the scanning mechanism 1. The detector control module 31 obtains, from the detector 8, the number n of fluorescence spectra each prepared per address (S207).

A process of S208 is executed in a similar manner to that of S108 in FIG. 11.

Then, the fluorescence characteristic management module 33 extracts each necessary feature variable from the fluorescence spectrum, which has been obtained from the detector 8, depending on the measurement object (S209). The fluorescence characteristic management module 33 extracts, for example, the "fluorescence intensity at a certain fluorescence wavelength".

Then, the fluorescence characteristic management module 33 stores, as the fluorescence characteristic data, not only the "scan position Yi", the "address Xi", and the "excitation light wavelength", which have been obtained from the relevant components, but also the "fluorescence wavelength" and the "fluorescence intensity", which have been extracted from the fluorescence spectrum by itself, in the fluorescence characteristic data storage unit 40 in correspondence to one another (S210).

Processes of S211 to S214 are executed in a similar manner to those of S110 to S113 in FIG. 11, respectively.

Then, the fluorescence characteristic analysis module 34 sorts the feature variable for each of the X- and Y-coordinates into the four classes based on the fluorescence characteristic data that is stored in the fluorescence characteristic data storage unit 40. Thereafter, the fluorescence characteristic analysis module 34 plots information of the sorted class for each cell on the two-dimensional map, which cell is specified by the X- and Y-coordinates, thereby preparing the map information (S215).

In accordance with the map information prepared by the fluorescence characteristic analysis module 34, the image preparation module 35 prepares a visualization image (such as illustrated in FIG. 15) to display the map information as a graph or a table on the display unit 24 (S216). Finally, the display unit 24 displays the visualization image (S217), which has been prepared by the image preparation module 35.

With the method described above, the visualization image representing the distribution of the fluorescent substance, illustrated in FIG. 15 as an example, is displayed on the display unit 24. From that image, the user can recognize the distribution of the fluorescent substance. By visualizing the distribution of the fluorescent substance specific to the blood vessel, for example, the shape of the blood vessel can be visualized.

[Modification]

In this embodiment, as in Embodiment 1, the fluorescence characteristic analysis module 34 may also compare two fluorescence spectra with each other, which are obtained by employing two types of excitation light sources 4 having different wavelengths, and by analyzing those two fluorescence spectra from a comprehensive point of view. As a result, the fluorescence characteristic analysis module 34 can measure the AGEs-derived fluorescent substance with higher accuracy.

In S215 of FIG. 16, the fluorescence characteristic analysis module 34 successively compares the feature variable obtained at the excitation light wavelength of 365 nm with the feature variable obtained at the excitation light wavelength of 405 nm for each scan position and for each address. The "feature target" as a comparison target is, for example, the "fluorescence intensity at the fluorescence wavelength of 460 nm". The fluorescence characteristic analysis module 34 executes the above-mentioned comparison for each scan position and for each address. Furthermore, the fluorescence characteristic analysis module 34 specifies the position information (X- and Y-coordinates) where a reduction of the fluorescence intensity at a reduction rate of about 45% (although the fluorescence intensity is not reduced down to 0) has been confirmed with the changing-over of the excitation light wavelength from 365 nm to 405 nm. Then, the fluorescence characteristic analysis module 34 assigns information (in the form of, e.g., a value, a mark or a flag), indicating that an AGEs-derived substance is contained, to the fluorescence characteristic data obtained at the X- and Y-coordinates where a reduction of the fluorescence intensity at a rate of about 45% has been confirmed, thereby reflecting such information on the map information.

The image preparation module 35 prepares the two-dimensional table, illustrated in FIG. 15, based on the above-described map information. In addition to preparing the graph, the image preparation module 35 prepares a visualization image in which the cell assigned with a flag indicating the AGEs-derived substance is displayed in a different color or highlighted to make the relevant cell recognized distinctively from other cells.

By looking at the visualization image thus prepared, the user can visually confirm the distribution of the AGEs-derived fluorescent substance with ease.

[Modification 2]

In this embodiment, by employing plural types of extracted feature variables, the fluorescence characteristic analysis module 34 may further prepare map information for each of the feature variables. Stated another way, the image preparation module 35 may prepare plural types of visualization images. Moreover, the image preparation module 35 may more finely display the distribution of the fluorescent substance in the measurement location by superimposing the plural types of prepared visualization images one on another.

A practical example of such a modification will be described below. The fluorescence characteristic analysis module 34 first prepares map information based on the fluorescence intensity at the fluorescence wavelength of 420 nm. In accordance with that map information, the image preparation module 35 prepares a visualization image representing shapes of blood vessels. The fluorescence characteristic analysis module 34 then prepares map information based on the fluorescence intensity at the fluorescence wavelength of 460 nm. In accordance with that map information, the image preparation module 35 prepares a visualization image representing a distribution of AGEs accumulated positions. Finally, the image preparation module 35 superimposes the visualization image representing the distribution of the AGEs accumulated positions on the visualization image representing the shapes of the blood vessels. Thus, the shapes of the blood vessels and the distribution of AGEs can be visualized on one image. By looking at such a superimposed visualization image, the user can more accurately recognize at which position of blood vessel walls AGEs are accumulated in what state. The reason why the blood vessels and AGEs can selectively be visualized by changing the feature variable (fluorescence wavelength) resides in that fluorescence characteristics of the fluorescent substance (elastin) contained in blood vessel walls differ from those of AGEs. Such a point will be described in more detail below.

A blood vessel wall is composed of about 70% of water and remaining 30% of elastin, collagen, and smooth muscle fibers. A composition ratio of elastin to collagen differs among the main artery, the other artery, and the vein. In the main artery, elastin exists about 1.5 times collagen at maximum. The ratio is about 0.5 in the other artery, and about 0.3 in the vein.

In other words, the position of the blood vessel wall and the type of blood vessel (main artery, artery or vein) in the measurement target having been subjected to the scan can be visualized by determining the amount and the position of elastin based on a fluorescence characteristic of elastin.

Figure 17:
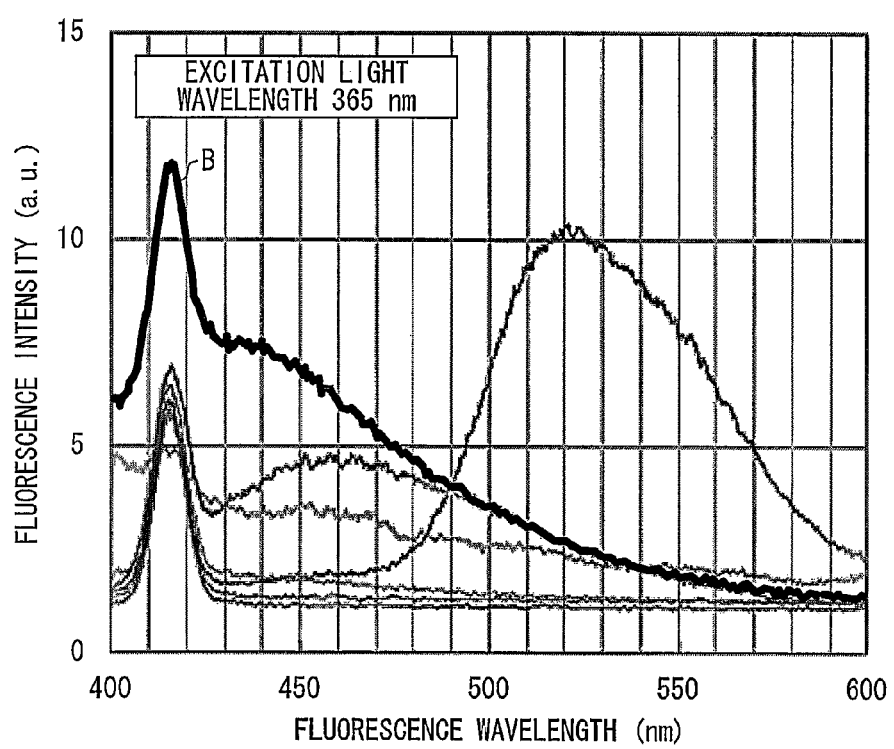
FIG. 17 is a graph depicting fluorescence spectra of various fluorescent substances when those fluorescent substances are irradiated with excitation light having a wavelength of 365 nm.

FIG. 17 is a graph depicting fluorescence spectra of various fluorescent substances when those fluorescent substances are irradiated with excitation light having a wavelength of 365 nm. Of the fluorescent spectra depicted in FIG. 17, a thick line B represents the fluorescent spectrum of the fluorescent substance "elastin".

As depicted in FIG. 17, the fluorescence characteristic of elastin is confirmed such that, when the excitation wavelength is 365 nm, elastin emits fluorescence having wavelength of 415 to 420 nm at much higher intensity than the other fluorescent substances. Accordingly, distributions of the amount and the position of elastin can be clarified by preparing map information based on the fluorescence intensity at the fluorescence wavelength of 420 nm with the aid of the fluorescence characteristic of elastin depicted in FIG. 17. Thus, the position of the blood vessel wall and the type of the blood vessel can be visualized.

On the other hand, FIG. 8 is a graph depicting a fluorescence spectrum of AGEs when the AGEs are irradiated with excitation light at a wavelength of 365 nm. As seen from FIG. 8, when the excitation wavelength is 365 nm, the AGEs emit fluorescence having fluorescence wavelength of 450 to 460 nm at maximum (peak) intensity. Accordingly, distributions of the amount and the position of AGEs can be clarified by preparing map information based on the fluorescence intensity at the fluorescence wavelength of 460 nm. Thus, the AGEs accumulated positions can be visualized.

Flow of a measurement process for visualizing blood vessel walls and AGEs by utilizing the above-described difference in optical characteristics between elastin and AGEs will be described below with reference to FIG. 18.

[Measurement Flow]

Figure 18:
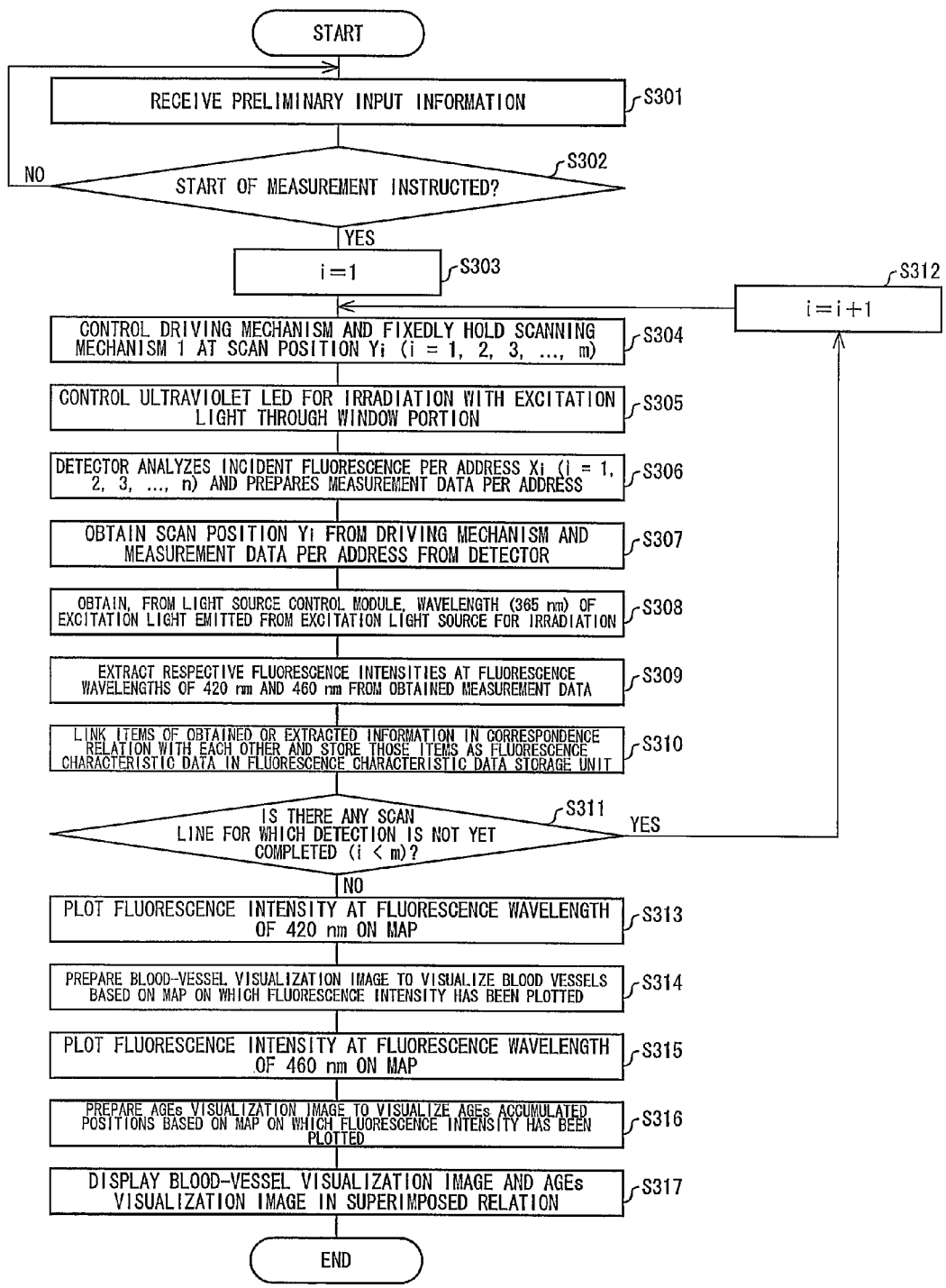
FIG. 18 is a flowchart illustrating flow of a measurement process for visualizing blood vessel walls and AGEs, the process being executed by various devices of the measuring system according to the other embodiment of the present invention.

FIG. 18 is a flowchart illustrating flow of the measurement process for visualizing blood vessel walls and AGEs, the process being executed by the various devices of the measuring system 100.

As illustrated in FIG. 18, the measuring device 9 first receives, via the operating unit 23, preliminary input information such as measurement conditions, measurement object, subject information, and information regarding the measurement location, i.e., information that is to be input from the user in advance (S301). It is here assumed that various measurement conditions for "examining the positions of blood vessels and the amounts of accumulated AGEs in the forearm of a human being" are input.

If a signal instructing the start of measurement is input via the operating unit 23 (YES in S302), the measuring device 9 controls the various components of the detecting device 10 to start a process of measuring the fluorescent substance in the measurement target that is rested on the window portion 3a.

First, the position information obtaining module 32 initializes the scan position Yi (i=1, 2, 3, . . . , m) (S303). Then, the position information obtaining module 32 controls the driving mechanism 2 and fixedly holds the scanning mechanism 1 at the scan position Yi (S304). When a scan is performed for the first time in the relevant measurement process, the scanning mechanism 1 is moved to the first scan position.

Then, the light source control module 30 controls the ultraviolet LED 4a of the excitation light source 4 for irradiation with the excitation light through the window portion 3a (S305). The excitation light reaches the measurement target (forearm) through the window portion 3a, and fluorescence radiated from the forearm enters the detector 8 through the fluorescence introducing portion 5 and the various components within the scanning mechanism 1. Thus, in this embodiment, the detector 8 receives the fluorescence per address for one scan line, analyzes the fluorescence per address Xi (i=1, 2, 3, . . . , n), and prepares measurement data (S306).

The position information obtaining module 32 obtains, from the stage controller 2b, the scan position Yi corresponding to the current position of the scanning mechanism 1. The detector control module 31 obtains the number n of fluorescence spectra prepared per address from the detector 8 (S307).

Then, the fluorescence characteristic management module 33 obtains the scan position Yi, the address Xi, and the fluorescence spectrum from the position information obtaining module 32 and the detector control module 31. Moreover, the fluorescence characteristic management module 33 obtains, from the light source control module 30, the wavelength (365 nm) of the excitation light used for the irradiation in the relevant measurement (S308). When only one type of excitation light is used in the relevant measurement, the above-described process may be omitted.

Then, the fluorescence characteristic management module 33 extracts each necessary feature variables from the fluorescence spectrum, which has been obtained from the detector 8, depending on the measurement object (S309). Here, the fluorescence characteristic management module 33 extracts, as the feature variables, the "fluorescence intensity at the fluorescence wavelength of 420 nm" and the "fluorescence intensity at the fluorescence wavelength of 460 nm".

Then, the fluorescence characteristic management module 33 links the "fluorescence intensity at the fluorescence wavelength of 420 nm" and the "fluorescence intensity at the fluorescence wavelength of 460 nm", which have been extracted from the fluorescence spectra by itself, in correspondence relation with the "scan position Yi" and the "address Xi", which have been obtained from the relevant components. Thereafter, the fluorescence characteristic management module 33 stores the thus-linked information, as fluorescence characteristic data, in the fluorescence characteristic data storage unit 40 (S310). Information of the "excitation light wavelength" may optionally be stored together.

Then, the position information obtaining module 32 determines whether the detection has been completed for all the scan positions (scan lines), or any scan line not yet subjected to the detection remains (S311).

If there remains a scan line for which the scan is not yet completed (YES in S311), the position information obtaining module 32 controls the driving mechanism 2 to advance the scan position Yi by one step (S312) and to move the scanning mechanism 1 to the next scan position (S304). Thereafter, the processes of S305 to S311 are repeated in the same procedures as those described above. The feature variables for each of all the scan positions and for each of all the addresses are then stored in the fluorescence characteristic data storage unit 40.

On the other hand, if the scan is completed for all the scan lines (NO in S311), the fluorescence characteristic analysis module 34 plots fluorescence intensity classes on a map based on the feature variable, representing the "fluorescence intensity at the fluorescence wavelength of 420 nm", among the fluorescence characteristic data that is stored in the fluorescence characteristic data storage unit 40, thereby preparing map information (S313). In accordance with the map information prepared by the fluorescence characteristic analysis module 34, the image preparation module 35 prepares a blood-vessel visualization image to visualize the shapes of the blood vessels (S314).

Then, the fluorescence characteristic analysis module 34 plots fluorescence intensity classes on a map based on the "fluorescence intensity at the fluorescence wavelength of 460 nm" among the fluorescence characteristic data that is stored in the fluorescence characteristic data storage unit 40, thereby preparing map information (S315). In accordance with the map information prepared by the fluorescence characteristic analysis module 34, the image preparation module 35 prepares an AGEs visualization image to visualize the positions and the shapes of accumulated AGEs (S316).

The image preparation module 35 displays, on the display unit 24, a superimposed image in which the prepared AGEs visualization image is superimposed on the prepared blood-vessel visualization image (S317).

Figure 19:
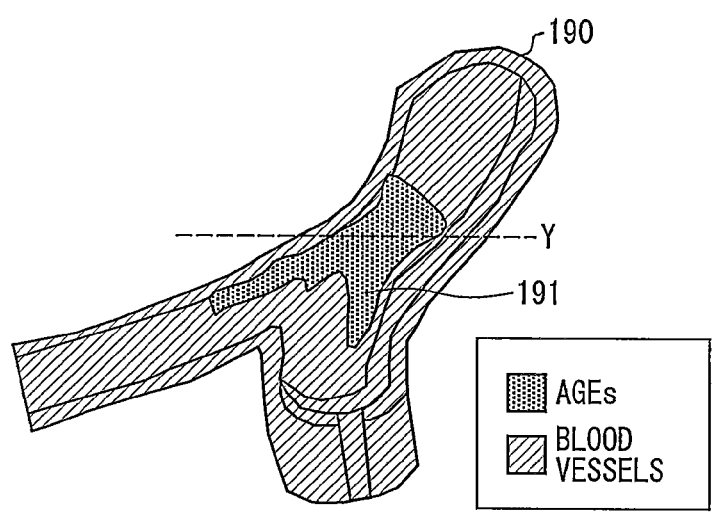
FIG. 19 illustrates one example of a superimposed image prepared by superimposing an AGEs visualization image on a blood-vessel visualization image.

FIG. 19 illustrates one example of the superimposed image prepared by superimposing the AGEs visualization image on the blood-vessel visualization image.

A hatched region 190 represents the blood vessels and the blood vessel walls, which are both visualized with the blood-vessel visualization image. A dotted region 191 represents the AGEs, which are visualized with the AGEs visualization image. As illustrated in FIG. 19, a visualization image enabling the user to understand at glance in what state AGEs are accumulated at which position in what type of blood vessel can be obtained by superimposing both the visualization images one on the other based on the position information.

With the method described above, the superimposed visualization image illustrated in FIG. 19, for example, is displayed on the display unit 24. As a result, the user can not only recognize the shapes and the positions of blood vessels, but also visually confirm in what state AGEs are accumulated at which position in what type of blood vessel.

As illustrated in FIG. 19, the image preparation module 35 may display the scan line (dotted line) and the coordinate (Y) of the scan position in addition to the superimposed image. Displaying the scan line and the coordinate enables the user to more accurately recognize the AGEs detected position.

Application Example

The measuring device 9, according to the present invention, for specifying the blood vessel position as described above can also be applied to fields described below.

In the measuring system 100 of the present invention, since the AGEs accumulated position can be specified by measuring the intensity of fluorescence generated from the measurement target with scanning over a plane, there is no necessity of specifying a position of irradiation with a probe in terms of a point unlike the related art. Therefore, it is no longer required to confirm the blood vessel position for the purpose of specifying a position where the probe is to be held.

However, recognizing the blood vessel position is still important in some other fields. For example, there are needs for measuring fluorescent substances (AGEs, collagen, etc.) all over a skin in a measurement target of a subject. A degree of aging of the skin can be recognized by measuring the accumulated amount of AGEs contained in the skin. A degree of skin resilience can also be recognized by measuring the amount of collagen. In those usages, the fluorescent substance existing in the blood vessel and radiating fluorescence at higher intensity than the skin causes noise.

In contrast, the measuring device 9 of the present invention can specify the blood vessel position and can eliminate, as noise, a fluorescence characteristic attributable to the blood vessel. Accordingly, the measurement of the fluorescent substance contained only in the skin can be performed with higher accuracy.

[Modifications]

While the foregoing embodiments have been each described in connection with the construction in which the scan position is changed by moving the scanning mechanism 1 that includes the excitation light source 4 and the fluorescence introducing portion 5, the detecting device 10 in the present invention is not limited to that construction. For example, when the scanning mechanism 1 is fixedly held, the scan position may be changed by moving the measurement target, or by moving the upper surface (window portion 3a) of the casing 3 while the measurement target is held standstill.

When the measurement target is moved, the scan position may be logically recognized by disposing, e.g., a pressure sensor around the window portion 3a (i.e., on the light shielding portion 3b) in the upper surface of the casing 3. The scan position is specified, for example, with the measurement target (e.g., the forearm) being placed on the light shielding portion 3b in the upper surface of the casing 3. An arm moving speed and the scan position can be determined by disposing a plurality of pressure sensors in a direction in which the arm is moved. Optical sensors may be disposed instead of the pressure sensors. The shape of the measurement target put on the casing 3 may be detected using infrared rays emitted from light sources in the optical sensors, and the scan position may be determined with movement of the measurement target.

While, in each of the foregoing embodiments, the driving mechanism 2 is described as moving the scanning mechanism 1 in one direction of the Y-axis, the driving mechanism 2 is not limited to that arrangement. For example, the driving mechanism 2 may move the scanning mechanism 1 to any desired position in two directions of the X-axis and the Y-axis. In such a case, the scanning mechanism 1 repeats detection for each point specified by X- and Y-coordinates, and supplies measurement data for each set of both the coordinates to the detector control module 31. On the other hand, the position information obtaining module 32 obtains, as position information, the scan position (Y-coordinate) and the address (X-coordinate) from the stage controller 2b. Such an arrangement can also enable the measurement target to be measured in terms of a plane.

[Modifications]

In each of the above-described embodiments, the detector 8 is supposed to be constructed such that CCD elements on a line have respective addresses (X-coordinate values) corresponding to the coordinates in the window portion 3a, and that 5400 photocells adapted for each wavelength (e.g., R, G or B) are arrayed. Accordingly, the detector 8 can accurately link the fluorescence reflected from the window portion 3a in correspondence relation with X-coordinate positions.

Figure 20:
FIG. 20 depicts a visualization image representing the contour of a measuring target (palm and wrist), the image being obtained by irradiating the measurement target with an ultraviolet LED.

The ultraviolet LED 4a may be used, instead of the visible light LED 4b, to obtain a visualization image representing the contour of a measurement target (e.g., an arm). FIG. 20 depicts a visualization image representing the contour of a measuring target (palm and wrist), the image being obtained by irradiating the measurement target with the ultraviolet LED 4a. In other words, when the detector 8 visualizes all lights of R, G and B, the contour of the measurement target can be visualized, as illustrated in FIG. 20, instead of visualizing the fluorescence at the particular wavelength, which is generated from blood vessels, for example.

Furthermore, a blood vessel is composed of elastin and collagen, and fluorescence wavelengths of those substances are inherently different from those of AGEs and NADH. Accordingly, an image of blood vessels and an image of accumulated AGEs can be obtained as two-dimensional visualization images by extracting optical feature variables per wavelength from the detected fluorescence with fine setting of wavelength.

In each of the above-described embodiments, the fluorescence spectrum is obtained in correspondence to the Y-coordinate position by moving the relative positions of the scanning mechanism 1 and the measurement target. However, the present invention is not limited to such an arrangement, and multipoint fluorescence detection of the measurement target may be performed in each of the above-described embodiments without driving the scanning mechanism 1 (i.e., by fixedly holding the relative positions of the scanning mechanism 1 and the measurement target).

In that case, since the relative positions of the scanning mechanism 1 and the measurement target are fixedly held, the fluorescence spectrum is analyzed in the measuring device 9 based on only the position information of the X-coordinate, which is output from the detector 8. For example, of signals having entered photocells of the detector 8, top ten signals descending from the signal having maximum fluorescence intensity may be averaged and then output as fluorescence intensity of AGEs.

The present invention is not limited to the above-described embodiments, and it may variously be modified within the scope defined in claims. Various embodiments obtained by appropriately combining the technical means disclosed in the above different embodiments with each other are also involved within the technical scope of the present invention.

Finally, the individual blocks of the measuring device 9, particularly the fluorescence characteristic management module 33 and the fluorescence characteristic analysis module 34, may be constituted with hardware logics, or may be realized with software by employing a CPU as follows.

The measuring device 9 includes a CPU (central processing unit) for executing commands of control programs for realizing various functions, a ROM (read only memory) storing the control programs, a RAM (random access memory) on which the control programs are developed, and a storage device (recording medium), such as a memory, for storing the control programs and various data. The object of the present invention can also be achieved by supplying, to the measuring device 9, a recording medium in which program code (including executive form programs, intermediate code programs, and source programs) of the control programs for the measuring device 9, i.e., software for realizing the above-described functions, is recorded in a state readable by a computer, and by causing the computer (or CPU or MPU) to read and execute the program code recorded in the recording medium.

The recording medium may be selected, for example, from among tapes such as a magnetic tape and a cassette tape, discs including magnetic discs such as a Floppy (registered trademark) disc and a hard disk, and optical discs such as CD-ROM, MO, MD, DVD, and CD-R, cards such as an IC card (including a memory card) and an optical card, and semiconductor memories such as mask ROM, EPROM, EEPROM and flash ROM.

The measuring device 9 may be connectable to a communication network such that the above-mentioned program code is supplied via the communication network. The communication network is not limited to particular one, and it may be practiced using, e.g., the Internet, an intranet, an extranet, LAN, ISDN, VAN, a CATV communication network, a virtual private network, a telephone network, a mobile communication network, or a satellite communication network. A transmission medium constituting the communication network is not limited to particular one, and it may be practiced, for example, in the wired form including IEEE1394, USB, power line transfer, a cable TV line, a telephone line, and an ADSL line, or in the wireless form including an infrared ray such as IrDA or remote control, Bluetooth (registered trademark), 802.11 wireless, HDR (High Data Rate), a cellular phone network, a satellite line, and a terrestrial digital network. It is to be noted that the present invention may also be realized when the above-described program code is practiced in the electronically transmitted form, i.e., in the form of a computer data signal buried in a carrier wave.

Stated another way, the present invention can be expressed as follows.

The present invention provides a measuring device featured in scanning a sensing mechanism including an excitation light irradiation unit for irradiating a living body with excitation light, and a light receiving unit for receiving fluorescence generated from the living body upon irradiation with the excitation light, and in visualizing the detected fluorescence as information at each scan position.

To solve the above-mentioned problem, the measuring device according to the present invention is capable of scanning the sensing mechanism including the excitation light irradiation unit for irradiating the living body with the excitation light, and the light receiving unit for receiving, as position information, fluorescence generated from the living body upon irradiation with the excitation light. With such an arrangement, biological information can be visualized based on the position information, and intravital fluorescence substances exhibiting different behaviors in different measurement locations or at different measurement positions can be detected as two-dimensional information. As well known, the detected fluorescence information includes physical property information attributable to the substances, such as information regarding fluorescence intensity, a wavelength at which the fluorescence is detected, and a half value width. Thus, positions where AGEs are detected in blood vessels can be visualized without employing an image sensing device for taking an image of a measurement target, such as a CCD (Charge Coupled Device) camera or a CMOS (Complementary Metal-Oxide-Semiconductor) camera. From experiments, it is confirmed that in, e.g., an arm, a wrist, an earlobe, a fingertip, a palm, and a cheek where blood vessels exist when a detection position is set there, the fluorescence intensity is increased in comparison with that at a position where no blood vessels exist. Accordingly, shapes of blood vessels in individual tissues can be visualized by visualizing information of the fluorescence intensity, and AGEs accumulated positions can also be monitored when the fluorescence intensity attributable to particular AGEs is confirmed at particular positions in the visualized blood vessels.

As another advantageous effect, variations in measurement error can be reduced by a signal processing technique of averaging the fluorescence intensity over a certain area or sampling several points, which exhibit top three values, from the fluorescence information obtained with scanning over a body surface.

The measuring device is featured in that the excitation light irradiation unit for irradiating the living body with the excitation light includes at least two excitation light sources, and that images obtained from fluorescence spectra using those light sources are superimposed one on the other. Moreover, the excitation light preferably includes two or more light sources to measure various AGEs.

With the above-described arrangement, AGEs and reduced nicotinamide adenine dinucleotide (NADH), i.e., a fluorescent molecule existing in the living body, can be measured separately from each other. Comparing the case using the excitation light of 365 nm for the detection and the case excited with the excitation light of 405 nm, AGEs exhibit the reduction of the fluorescence intensity at a rate of about 45% with the changing-over of the excitation light to the longer wavelength. In contrast, fluorescence generated from NADH, which is famous as an intravital fluorescence molecule, is hardly detected on the same conditions when NADH is excited with the excitation light of 405 nm. It is also known that NADH usually considerably absorbs an ultraviolet ray of 340 nm. Thus, AGEs and the other background substance can be separately identified by changing over the excitation light. Such separation is also realized with the above-described arrangement by scanning the sensing mechanism while the light sources (e.g., 365 nm and 405 nm) are changed over, and by obtaining two types of images with one scan. The positions where AGEs exist can more accurately be visualized by comparing those two types of images with each other.

The above-mentioned excitation light preferably has a wavelength range adapted for measuring Advanced Glycation Endproducts.

Advanced Glycation Endproducts can be measured with the above-described arrangement. The inventors of the present invention have found that, when a measurement target is irradiated with excitation light having wavelength adapted for measuring Advanced Glycation Endproducts, the intensity of fluorescence generated from the measurement target greatly differs depending on irradiation positions of the excitation light. Accordingly, the present invention is usefully practiced as a measuring device for measuring Advanced Glycation Endproducts.

The following arrangements are further involved within the scope of the present invention.

To solve the above-mentioned problem, a measuring device according to the present invention comprises measurement data obtaining means for obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence, position information obtaining means for obtaining, from a driving mechanism for controlling relative positions of the scanning mechanism and the measurement target, position information indicating an irradiation position where the measurement target is irradiated with the excitation light when the measurement data is obtained, and fluorescence characteristic management means for preparing fluorescence characteristic data including the measurement data obtained by the measurement data obtaining means and the position information obtained by the position information obtaining means.

The fluorescence characteristic management means preferably prepares, each time the relative positions are changed, the fluorescence characteristic data per the position information corresponding to the relevant relative positions.

Preferably, the measuring device further comprises fluorescence characteristic analysis means for preparing map information by plotting the measurement data on a map based on the position information included in the fluorescence characteristic data, and image preparation means for preparing a visualization image to display the map information on a display unit.

With the above-described arrangement, the fluorescence characteristic analysis means collates the fluorescence characteristic data stored each time the relative positions are changed, thus mapping the measurement data based on the position information. Furthermore, the image preparation means visualizes the mapped measurement data such that a user can visually confirm the measurement data.

As a result, by looking at the visualization image, the user can promptly and easily recognize in which region of a surface of the measurement target the fluorescence intensity is strong at which wavelength.

The position information included in the fluorescence characteristic data may be one-dimensional information (e.g., a scan position Y described later) for specifying a Y-coordinate of the irradiation position in the measurement target.

With such a feature, the user can fairly recognize, in terms of the Y-coordinate, at which scan position a fluorescent substance is detected in large amount. In addition, the user can perform more detailed measurement by focusing on the relevant scan position, or can observe the progress with the lapse of time.

Alternatively, the position information included in the fluorescence characteristic data may be two-dimensional information (e.g., a scan position Y and an address X described later) for specifying X- and Y-coordinates of the irradiation position in the measurement target.

With such a feature, the user can promptly recognize fluorescence characteristics over the entire surface of the measurement target.

Preferably, the excitation light irradiation unit includes plural types of light sources having different excitation wavelengths, the measurement data obtaining means obtains measurement data that differs per the excitation wavelength, and the fluorescence characteristic management means prepares the fluorescence characteristic data per the position information and per the excitation wavelength.

Preferably, the measuring device further comprises fluorescence characteristic analysis means for preparing map information per the excitation wavelength by plotting the measurement data on a map based on the position information included in the fluorescence characteristic data, and image preparation means for preparing a visualization image to display the map information on a display unit, wherein the fluorescence characteristic analysis means compares, per the position information, the measurement data linked in correspondence relation with a first excitation wavelength and the measurement data linked in correspondence relation with a second excitation wavelength for each fluorescence characteristic data, and assigns the plotted measurement data with information indicating that a comparison result of both the measurement data satisfies a predetermined condition, and the image preparation means prepares the visualization image in a way of highlighting the measurement data assigned with the aforesaid information.

There is a fluorescent substance exhibiting peculiar change in fluorescence characteristics when the fluorescent substance is irradiated with different excitation wavelengths. With the above-described arrangement, it is possible to easily identify the fluorescent substance having such a peculiar property by comparing the fluorescence characteristics at different excitation wavelengths with each other, and to easily specify the position where the peculiar change appears, i.e., the position where the identified fluorescent substance exists.

The first excitation wavelength and the second excitation wavelength preferably have respective wavelength ranges adapted for measuring Advanced Glycation Endproducts. More specifically, it is preferable that the first excitation wavelength is 365 nm and the second excitation wavelength is 405 nm.

With the above-described features, when an objective fluorescent substance (Advanced Glycation Endproducts) and an a fluorescent substance (NADH) existing as noise are contained in a region where fluorescence strongly appears, only the position where AGEs exist can be visualized by separately removing the noise.

The fluorescence characteristic management means may extract, as a feature variable, fluorescence intensity at a particular fluorescence wavelength from the measurement data, and may prepare the fluorescence characteristic data including the position information and the feature variable.

The measuring device may further comprise fluorescence characteristic analysis means for preparing map information per the fluorescence wavelength by plotting the feature variable on a map based on the position information included in the fluorescence characteristic data, and image preparation means for preparing a visualization image to display the map information on a display unit, wherein the image preparation means may prepare the visualization image by superimposing the map information based on a first feature variable representing fluorescence intensity at a first fluorescence wavelength and the map information based on a second feature variable representing fluorescence intensity at a second fluorescence wavelength.

With those features, respective shapes of a first organ (or a substance), which exists in the measurement target and which can be visualized using the first feature variable, and a second organ (or a substance), which can be visualized using the second feature variable, can be visualized in a synthetic imaging manner.

An excitation wavelength of the excitation light irradiation unit, the first fluorescence wavelength, and the second fluorescence wavelength preferably have respective wavelength ranges adapted for measuring Advanced Glycation Endproducts existing in blood vessels and for specifying positions thereof. More specifically, it is preferable that the excitation wavelength is 365 nm, the first fluorescence wavelength is 420 nm, and the second fluorescence wavelength is 460 nm.

With those features, when the excitation wavelength is 365 nm and the first fluorescence wavelength is 420 nm, shapes of blood vessels can be visualized, and when the excitation wavelength is 365 nm and the second fluorescence wavelength is 460 nm, Advanced Glycation Endproducts can be visualized.

As a result, it is possible to not only visualize a region where fluorescence strongly appears, but also to visualize at which position in blood vessels and in what amount Advanced Glycation Endproducts exist.

The fluorescence generated from blood vessel tissues in the measurement target, which is excited using the excitation light irradiation unit, is fluorescence attributable to Advanced Glycation Endproducts (AGEs), and the Advanced Glycation Endproducts are accumulated by a physiological reaction in the living body.

In other words, the measuring device of the present invention can obtain, by employing the above-described scanning mechanism, the measurement data regarding AGEs accumulated in the blood vessels in the measurement target. Thus, the measuring device can obtain data regarding an inherent state of a living body, i.e., data having high correlation with respect to the function of the vascular endothelial and the situations in progress of diseases, by detecting AGEs from the blood vessels in a non-invasive manner. As a result, a measuring device allowing anybody to readily monitor the health condition on a daily basis can be realized.

A measuring system constructed of the above-described measuring device, scanning mechanism, and driving mechanism is also involved within the scope of the present invention.

The measuring device may be realized with a computer. In such a case, a control program for the measuring device, the control program causing a computer to operate as the above-described individual means, thus realizing the measuring device with the computer, and a computer-readable recording medium recording the control program are further involved within the scope of the present invention.

INDUSTRIAL APPLICABILITY

According to the measuring device of the present invention, a measuring device, which enables anybody to readily employ it with high accuracy and which has not been obtained with the related art, can be realized free from taking care of variations in irradiation position for each measurement without requiring an additional visualization mechanism. The measuring device of the present invention can suitably be used as a health condition monitoring device to readily monitor the health condition at home in forthcoming preventive health-care society. Particularly, in consideration of high needs for preventive health-care against circulatory diseases, the measuring device of the present invention capable of readily monitoring AGEs, which may be accumulated on blood vessel walls and may cause arteriosclerosis etc., is suitably used as an adult disease preventive device and a skin-care monitoring device.

REFERENCE SIGNS LIST 1 scanning mechanism
2 driving mechanism
2a motor-operated stage
2b stage controller
3 housing
3a window portion
3b light shielding portion
4 excitation light source (excitation light irradiation unit)
4a ultraviolet LED (excitation light irradiation unit)
4b visible light LED (excitation light irradiation unit)
5 fluorescence introducing portion (light receiving unit)
6 light guiding member (light receiving unit)
7 lens (light receiving unit)
8 detector (light receiving unit)
9 measuring device
10 detecting device
20 control unit
21 storage unit
22 communication unit
23 operating unit
24 display unit
30 light source control module
31 detector control module (measurement data obtaining means)
32 position information obtaining module (position information obtaining means)
33 fluorescence characteristic management module (fluorescence characteristic management means)
34 fluorescence characteristic analysis module
35 (fluorescence characteristic analysis means)
35 image preparation module (image preparation means)
40 fluorescence characteristic data storage unit
100 measuring system

The invention claimed is:

1. A measuring device, comprising:
measurement data obtaining means for obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence;
position information obtaining means for obtaining, from a driving mechanism for controlling relative positions of the scanning mechanism and the measurement target, position information indicating an irradiation position where the measurement target is irradiated with the excitation light when the measurement data is obtained;
fluorescence characteristic management means for extracting, as a feature variable, fluorescence intensity at a particular florescence wavelength from the measurement data, and for preparing fluorescence characteristic data including the position information and the feature variable;
fluorescence characteristic analysis means for preparing map information by plotting the feature variable on a map based on the position information; and
image preparation means for preparing a visualization image to display the map information on a display unit,
wherein the excitation light irradiation unit includes plural types of light sources having different excitation wavelengths,
the measurement data obtaining means obtains measurement data that differs per the excitation wavelength,
the fluorescence characteristic management means prepares the fluorescence characteristic data per the position information and per the excitation wavelength,
the fluorescence characteristic analysis means compares, per the position information, fluorescence intensity in the measurement data linked in correspondence relation with a first excitation wavelength and fluorescence intensity in the measurement data linked in correspondence relation with a second excitation wavelength, and assigns information indicating that a result of the comparison satisfies a predetermined condition to the feature variable plotted at a position indicated by the position information, and
the image preparation means prepares the visualization image in a way of highlighting the feature variable to which the information is assigned.

2. The measuring device according to claim 1, wherein the fluorescence characteristic management means prepares, each time the relative positions are changed, the fluorescence characteristic data per the position information corresponding to the relevant relative positions.

3. The measuring device according to claim 1, wherein the position information included in the fluorescence characteristic data is one-dimensional information for specifying a Y-coordinate of the irradiation position in the measurement target.

4. The measuring device according to claim 1, wherein the position information included in the fluorescence characteristic data is two-dimensional information for specifying X- and Y-coordinates of the irradiation position in the measurement target.

5. The measuring device according to claim 1, wherein the first excitation wavelength and the second excitation wavelength have respective wavelength ranges adapted for measuring Advanced Glycation Endproducts.

6. The measuring device according to claim 1, wherein the first excitation wavelength is 365 nm and the second excitation wavelength is 405 nm.

7. The measuring device according to claim 1,
wherein the fluorescence characteristic management means extracts, a first feature variable representing intensity at a first fluorescence wavelength and a second feature variable representing fluorescence intensity at a second-florescence wavelength;
the image preparation means prepares the visualization image by superimposing the map information based on the first feature variable and the map information based on the second feature variable.

8. The measuring device according to claim 7, wherein an excitation wavelength of the excitation light irradiation unit, the first fluorescence wavelength, and the second fluorescence wavelength have respective wavelength ranges adapted for measuring Advanced Glycation Endproducts existing in blood vessels and specifying positions thereof.

9. The measuring device according to claim 7, wherein the excitation wavelength is 365 nm, the first fluorescence wavelength is 420 nm, and the second fluorescence wavelength is 460 nm.

10. The measuring device according to claim 1, wherein the fluorescence generated from blood vessel tissues in the measurement target, which is excited by the excitation light irradiation unit, is fluorescence attributable to Advanced Glycation Endproducts (AGEs), and the Advanced Glycation Endproducts are accumulated by a physiological reaction in the living body.

11. A measuring system, comprising:
a scanning mechanism including an excitation light irradiation unit for irradiating a measurement target with excitation light, and a light receiving unit for receiving fluorescence generated from the measurement target upon irradiation with the excitation light;
a driving mechanism for controlling relative positions of the scanning mechanism and the measurement target; and
a measuring device according to claim 1, the measuring device communicating with the scanning mechanism and the driving mechanism.

12. A non-transitory computer-readable recording medium recording a control program for causing a computer to function as the individual means of the measuring device according to claim 1.

13. A measuring method, comprising:
a measurement data obtaining step of obtaining, from a scanning mechanism including an excitation light irradiation unit for irradiating a measurement target with excitation light and a light receiving unit for receiving fluorescence generated from the measurement target upon irradiation with the excitation light, measurement data representing optical characteristics of the fluorescence;
a position information obtaining step of obtaining, from a driving mechanism for controlling relative positions of the scanning mechanism and the measurement target, position information indicating an irradiation position where the measurement target is irradiated with the excitation light when the measurement data is obtained; and
a fluorescence characteristic management step of extracting, as a feature variable, fluorescence intensity at a particular florescence wavelength from the measurement data, and of preparing fluorescence characteristic data including the feature variable and the position information,
a fluorescence characteristic analysis step of preparing map information by plotting the feature variable on a map based on the position information; and
an image preparation step of preparing a visualization image to display the map information on a display unit,
wherein the excitation light irradiation unit includes plural types of light sources having different excitation wavelengths,
in the measurement data obtaining step, measurement data that differs per the excitation wavelength is obtained,
in the fluorescence characteristic management step, the fluorescence characteristic data is prepared per the position information and per the excitation wavelength,
in the fluorescence characteristic analysis step, fluorescence intensity in the measurement data linked in correspondence relation with a first excitation wavelength and fluorescence intensity in the measurement data linked in correspondence relation with a second excitation wavelength are compared with each other per the position information, and information indicating that a result of the comparison satisfies a predetermined condition is assigned to the feature variable plotted at a position indicated by the position information, and
in the image preparation step, the visualization image is prepared in a way of highlighting the feature variable to which the information is assigned.

* * * * *